United States Patent
Matsukawa et al.

(10) Patent No.: US 6,352,847 B1
(45) Date of Patent: Mar. 5, 2002

(54) AMMONIA ELIMINATION LIQUID REAGENT

(75) Inventors: Hirokazu Matsukawa, Osaka-fu; Osamu Oka, Kyoto-fu; Tuyosi Fujita, Osaka-fu; Kentaro Miyazaki, Kanagawa-ken, all of (JP)

(73) Assignee: Japan as represented by Director General of Agency of Industrial Science and Technology (JP)

( * ) Notice: Subject to any disclaimer, the term of this patent is extended or adjusted under 35 U.S.C. 154(b) by 0 days.

(21) Appl. No.: 09/327,487

(22) Filed: Jun. 8, 1999

(30) Foreign Application Priority Data

Jun. 9, 1998 (JP) .............................. 10-176643

(51) Int. Cl.[7] .............................. C12N 9/04; C12Q 1/32; A61K 38/44
(52) U.S. Cl. .................... 435/190; 435/26; 424/94.4
(58) Field of Search .................. 435/26, 190; 424/94.4

(56) References Cited

U.S. PATENT DOCUMENTS

| | | | |
|---|---|---|---|
| 5,871,948 A | 2/1999 | Matsukawa et al. | 435/26 |
| 5,888,766 A | 3/1999 | Ishizuka et al. | 435/69.1 |

FOREIGN PATENT DOCUMENTS

| | | | |
|---|---|---|---|
| EP | 0750046 A1 | * 12/1996 | |
| EP | 0 750 046 A1 | 12/1996 | |
| JP | 63-214182 | 9/1988 | |
| JP | 8-103278 | 4/1996 | |
| JP | 8-103279 | 4/1996 | |
| JP | 9-295 | 1/1997 | |
| JP | 10-165181 | 6/1998 | |

OTHER PUBLICATIONS

Catalog of Dojin Chemical Research Institute (19th Edition, 1994), p. 355.

Miyazaki, "Isocitrate Dehydrogenase from *Thermus aquaticus* YT1: Purification of the Enzyme and Cloning, Sequencing, and Expression of the Gene", Appl. Environ. Microbiol., vol. 62, No. 12, 4627–31, 1996.

Ramaley, R. et al., Biochem. Biophys. Acta, vol. 315, No.1, pp. 22–36, 1973.*

* cited by examiner

*Primary Examiner*—Ponnathapu Achutamurthy
*Assistant Examiner*—Peter Tung
(74) *Attorney, Agent, or Firm*—Burns, Doane, Swecker, & Mathis, L.L.P.

(57) ABSTRACT

The invention provides an ammonia elimination reagent in solution, comprising a thermo-resistant isocitrate dehydrogenase with prominent stability under conditions at high alkaline pHs. For example, the isocitrate dehydrogenase is preferably derived from the genus Thermus. For an assay system of biological substances generating a reaction product ammonia, an ammonia elimination reagent can be prepared by selecting and using the enzyme; the resulting ammonia elimination reagent can be stored in solution; additionally, the assay system can be designed in combination with both the coenzymes $NAD^+$ and $NADP^+$. The ammonia elimination reagent is novel and can eliminate ammonia in an extremely short time.

6 Claims, 5 Drawing Sheets

Control 1; JP8-328400 by batch culture and high-density culture
Control 2; pTRP recombinant by batch culture
Invention; pTRP recombinant by high-density culture

SEQUENCE LISTING

<160> NUMBER OF SEQ ID NOS: 7

<210> SEQ ID NO 1
<211> LENGTH: 426
<212> TYPE: PRT
<213> ORGANISM: Thermus aquaticus

<400> SEQUENCE: 1

Met Ala Tyr Gln Arg Ile Gln Ile Pro Gln Glu Gly Glu Lys Ile Thr
1               5                  10                  15

Ile Gln Glu Gly Val Leu Lys Val Pro Asp Gln Pro Ile Ile Gly Phe
        20                  25                  30

```
Ile Glu Gly Asp Gly Thr Gly Pro Asp Ile Trp Arg Ala Ala Gln Pro
        35                  40                  45

Val Leu Asp Ala Ala Val Ala Lys Ala Tyr Gly Gly Gln Arg Arg Ile
    50                  55                  60

Val Trp Val Glu Leu Tyr Ala Gly Glu Lys Ala Asn Gln Val Tyr Gly
65                  70                  75                  80

Glu Pro Ile Trp Leu Pro Glu Glu Thr Leu Glu Phe Ile Arg Glu Tyr
                85                  90                  95

Leu Val Ala Ile Lys Gly Pro Leu Thr Thr Pro Val Gly Gly Gly Ile
                100                 105                 110

Arg Ser Ile Asn Val Ala Leu Arg Gln Glu Leu Asp Leu Tyr Ala Cys
            115                 120                 125

Val Arg Pro Val Arg Trp Phe Gln Gly Val Pro Ser Pro Val Lys His
    130                 135                 140

Pro Glu Leu Val Asn Met Val Ile Phe Arg Glu Asn Thr Glu Asp Ile
145                 150                 155                 160

Tyr Ala Gly Ile Glu Trp Pro Ala Gly Ser Glu Glu Val Lys Lys Val
                165                 170                 175

Leu Asp Phe Leu Lys Arg Glu Phe Pro Lys Ala Tyr Ala Lys Ile Arg
                180                 185                 190

Phe Pro Glu Thr Ser Gly Leu Gly Leu Lys Pro Ile Ser Lys Glu Gly
            195                 200                 205

Thr Glu Arg Leu Val Glu Ala Ala Ile Glu Tyr Ala Ile Lys Glu Asp
    210                 215                 220

Leu Pro Ser Val Thr Leu Val His Lys Gly Asn Ile Met Lys Phe Thr
225                 230                 235                 240

Glu Gly Ala Phe Arg Glu Trp Gly Tyr Ala Leu Ala Arg Glu Lys Tyr
                245                 250                 255

Gly Ala Thr Pro Leu Asp Gly Pro Trp His Val Leu Lys Asn Pro
                260                 265                 270

Arg Thr Gly Arg Glu Ile Val Ile Lys Asp Met Ile Ala Asp Asn Phe
            275                 280                 285

Leu Gln Gln Ile Leu Leu Arg Pro Asp Glu Tyr Ser Val Ile Ala Thr
    290                 295                 300

Met Asn Leu Asn Gly Asp Tyr Ile Ser Asp Ala Leu Ala Ala Gln Val
305                 310                 315                 320

Gly Gly Ile Gly Ile Ala Pro Gly Ala Asn Ile Asn Tyr Lys Thr Gly
                325                 330                 335

His Ala Val Phe Glu Ala Thr His Gly Thr Ala Pro Lys Tyr Ala Gly
                340                 345                 350

Gln Asp Lys Val Asn Pro Ser Ser Val Ile Leu Ser Gly Glu Met Met
            355                 360                 365

Leu Arg Tyr Leu Gly Trp Asn Glu Ala Ala Asp Leu Ile Ile Arg Ala
    370                 375                 380

Met Glu Arg Thr Ile Ser Lys Gly Leu Val Thr Tyr Asp Phe His Arg
385                 390                 395                 400

Leu Leu Val Ala Glu Gly Lys Pro Ala Thr Leu Leu Lys Thr Ser Glu
                405                 410                 415

Phe Gly Gln Ala Leu Ile Gln His Met Asp
            420                 425

<210> SEQ ID NO 2
<211> LENGTH: 2872
<212> TYPE: DNA
```

-continued

<213> ORGANISM: Thermus aquaticus
<220> FEATURE:
<221> NAME/KEY: CDS
<222> LOCATION: (180)..(1460)

<400> SEQUENCE: 2

```
gctccttccc gtggacccct gggcgaaggt ggcctccttc tccaaaagga ggaccttaag        60
ccccgcctcc gctagccggt aggccgaggc cgccccctacg atccccgccc ccaccaccag       120
cacatccgcc acctccccag tttaggaagc cgggagtatg ctaggccccg gaggtacct        179 atg gcc tac cag cgc atc cag att ccc cag gag ggc gaa aag atc acc        227
Met Ala Tyr Gln Arg Ile Gln Ile Pro Gln Glu Gly Glu Lys Ile Thr
 1               5                  10                  15 atc caa gag ggc gtc ctg aag gtg ccg gac cag ccc atc atc ggc ttc        275
Ile Gln Glu Gly Val Leu Lys Val Pro Asp Gln Pro Ile Ile Gly Phe
             20                  25                  30 att gag ggg gat ggg acc ggc cct gac atc tgg aga gcg gcc caa ccc        323
Ile Glu Gly Asp Gly Thr Gly Pro Asp Ile Trp Arg Ala Ala Gln Pro
         35                  40                  45 gtc cta gac gcc gcc gtg gcc aaa gcc tac ggc ggg caa cgc gcc atc        371
Val Leu Asp Ala Ala Val Ala Lys Ala Tyr Gly Gly Gln Arg Arg Ile
     50                  55                  60 gtc tgg gtg gag ctt tac gcc ggg gaa aag gcc aac cag gtc tac ggg        419
Val Trp Val Glu Leu Tyr Ala Gly Glu Lys Ala Asn Gln Val Tyr Gly
 65                  70                  75                  80 gag ccc atc tgg ctc ccc gag gag acc ctg gag ttc atc cgg gag tac        467
Glu Pro Ile Trp Leu Pro Glu Glu Thr Leu Glu Phe Ile Arg Glu Tyr
                 85                  90                  95 ctg gtg gcc atc aag ggc ccc ctg acc acg ccg gtg ggc ggc ggc atc        515
Leu Val Ala Ile Lys Gly Pro Leu Thr Thr Pro Val Gly Gly Gly Ile
             100                 105                 110 cgg agc atc aac gtg gcc ctc agg cag gag ctg gac ctc tac gcc tgc        563
Arg Ser Ile Asn Val Ala Leu Arg Gln Glu Leu Asp Leu Tyr Ala Cys
         115                 120                 125 gtg cgc ccc gtg cgc tgg ttc cag ggg gtg ccc agt ccg gtg aag cac        611
Val Arg Pro Val Arg Trp Phe Gln Gly Val Pro Ser Pro Val Lys His
     130                 135                 140 ccg gag ctg gtc aac atg gtc atc ttc cgg gag aac acc gag gac atc        659
Pro Glu Leu Val Asn Met Val Ile Phe Arg Glu Asn Thr Glu Asp Ile
145                 150                 155                 160 tac gcc ggg att gag tgg ccg gcg ggg agc gag gag gta aag aag gtc        707
Tyr Ala Gly Ile Glu Trp Pro Ala Gly Ser Glu Glu Val Lys Lys Val
                 165                 170                 175 cta gac ttc ttg aag cgg gag ttc ccc aag gcc tac gcc aag atc cgc        755
Leu Asp Phe Leu Lys Arg Glu Phe Pro Lys Ala Tyr Ala Lys Ile Arg
             180                 185                 190 ttc ccc gag acc tcg ggc ctg ggc ctg aag ccc atc tcc aag gag ggc        803
Phe Pro Glu Thr Ser Gly Leu Gly Leu Lys Pro Ile Ser Lys Glu Gly
         195                 200                 205 acg gag cgc ctg gtg gag gcg gcc att gag tac gcc atc aag gag gac        851
Thr Glu Arg Leu Val Glu Ala Ala Ile Glu Tyr Ala Ile Lys Glu Asp
     210                 215                 220 ctc ccc agc gtg acc ctg gtc cac aaa ggc aac atc atg aag ttc acc        899
Leu Pro Ser Val Thr Leu Val His Lys Gly Asn Ile Met Lys Phe Thr
225                 230                 235                 240 gaa ggg gcc ttc cgg gag tgg ggc tac gcc ctg gcc cgg gaa aag tac        947
Glu Gly Ala Phe Arg Glu Trp Gly Tyr Ala Leu Ala Arg Glu Lys Tyr
                 245                 250                 255
```

-continued

| | |
|---|---|
| ggg gcc acg ccc ctg gag ggc ggg ccc tgg cac gtc ctc aaa aac ccc<br>Gly Ala Thr Pro Leu Glu Gly Gly Pro Trp His Val Leu Lys Asn Pro<br>260               265               270 | 995 |
| cgc acc ggc agg gag atc gtt atc aag gac atg atc gcc gac aac ttc<br>Arg Thr Gly Arg Glu Ile Val Ile Lys Asp Met Ile Ala Asp Asn Phe<br>275               280               285 | 1043 |
| ctg cag cag atc ctc ctc cgc ccc gac gaa tac tcg gtg atc gcc acc<br>Leu Gln Gln Ile Leu Leu Arg Pro Asp Glu Tyr Ser Val Ile Ala Thr<br>290               295               300 | 1091 |
| atg aac ctg aac ggg gac tac atc tcc gat gcc ctg gcc gcc cag gtg<br>Met Asn Leu Asn Gly Asp Tyr Ile Ser Asp Ala Leu Ala Ala Gln Val<br>305               310               315               320 | 1139 |
| ggg ggc atc ggc atc gcc ccc ggg gcc aac atc aac tac aag acg ggc<br>Gly Gly Ile Gly Ile Ala Pro Gly Ala Asn Ile Asn Tyr Lys Thr Gly<br>325               330               335 | 1187 |
| cac gcc gtc ttt gag gcc acc cac ggc acc gcc ccc aag tac gct ggc<br>His Ala Val Phe Glu Ala Thr His Gly Thr Ala Pro Lys Tyr Ala Gly<br>340               345               350 | 1235 |
| cag gac aag gtg aac ccc agc agc gtc atc ctc tcc ggg gag atg atg<br>Gln Asp Lys Val Asn Pro Ser Ser Val Ile Leu Ser Gly Glu Met Met<br>355               360               365 | 1283 |
| ctt cgc tac ctg ggc tgg aac gag gcg gcg gac ctc atc atc agg gcc<br>Leu Arg Tyr Leu Gly Trp Asn Glu Ala Ala Asp Leu Ile Ile Arg Ala<br>370               375               380 | 1331 |
| atg gag agg acc atc agc aag ggc ctg gtc acc tac gac ttc cac cgc<br>Met Glu Arg Thr Ile Ser Lys Gly Leu Val Thr Tyr Asp Phe His Arg<br>385               390               395               400 | 1379 |
| ctc ctg gtg gcc gag ggc aag ccc gcc acg ctt ctt aag acc agc gag<br>Leu Leu Val Ala Glu Gly Lys Pro Ala Thr Leu Leu Lys Thr Ser Glu<br>405             410               415 | 1427 |
| ttc ggc cag gcc ctg atc cag cac atg gac tga aaacgtttgg ggccccgcc<br>Phe Gly Gln Ala Leu Ile Gln His Met Asp<br>420               425 | 1480 |
| gtggcaaaag ccacggcggg gtgcttagac cagggcgaag cgggcctcga ggccggaag | 1540 |
| gtccgcctcc aggaagcgga ggcggacctc ggcgttgagg gcaagaggcc cggagagggc | 1600 |
| cacctgggcg gaaagcccga gctccgggag gaggaagacc ccctgtcccc ccggcctctc | 1660 |
| caccaggacg cccgggccct cgtagccctt ttccatcagg taggagggg tccagtggag | 1720 |
| cttgctccgc ctctcccctt cccgcaccag gtcggccacc gcctccgccg ccccacccg | 1780 |
| ctccaggacc tccccctggg aaagggggcct ttccccccttg agccaggccc tgagctgctg | 1840 |
| gtgagccacc aggtccaggt agcgccttaa ggggctcgtc acctgggcgt agaggggaag | 1900 |
| gccgaggccc cggtgggggg cgggacggc cttgagctgc gccctcttca gggtcttccg | 1960 |
| ctgcgcccac atggcggcga ggccctcccc ctccacccgg tgggaagggg cctcctgggt | 2020 |
| ggcgaaggga aagggaaggc cctccctcag ggccaggtgg gcggcgcgta ggcgaaggag | 2080 |
| catggcctcc cgcacccaga cccggctttt atagggggga aggggggtga tccggatctc | 2140 |
| ctcccctcc acccgaacct tgacctcggg caggcgatg tccaaagccc cctgggccag | 2200 |
| gcgcttccga aaaagtccc ccgccaaggc cttcatgggc gccagggcct ccacctcgag | 2260 |
| ggctcccggt agaaagccgc ctcacccgca cccaggagag gtaaaggtcc tcccgcaaaa | 2320 |
| ggctccttcc ggggagacca gaagctcaaa ggtgagggct ggggagacct ccttaagccc | 2380 |
| cagcccaggg cctcggtcac cgccaggggg agcatgggca ccgtgccctc gggcagatag | 2440 |
| aggttggccc cccggcggag ggcctcctgg tccaggggc ttcccggccc gaccaaagcg | 2500 |
| gccacatcgg ccacatggac gaaaaggtgg aagccctcct ccaccctttc ggcgtaaagg | 2560 |

-continued

```
gcgtcgtccg ggtcctggct cccctcgtcg tcaatggcga aggcggggag gtgggtgagg    2620
tccacccgct cctcctcggg caggggggg acggggaggt ccggcggggc cagggaagg    2680 ccaagccgcc tggggtgggg gttttcccgc cgccagaggc ccaggcggag aaggagccgt    2740 ggcggcctc gggggtttcg ggaaggccca gggccttgag aagccggctt tccttcctct    2800
cgccgtgggc cagagcctcc acctcggcca ggagggggcg gtcctcgagg gagggccgtc    2860
cctggcggat cc                                                        2872
```

```
<210> SEQ ID NO 3
<211> LENGTH: 1281
<212> TYPE: DNA
<213> ORGANISM: Thermus aquaticus
<220> FEATURE:
<221> NAME/KEY: CDS
<222> LOCATION: (1)..(1281)

<400> SEQUENCE: 3
```

| | | |
|---|---|---|
| atg gct tac cag cgc atc cag att ccg cag gag ggc gaa aag atc acc<br>Met Ala Tyr Gln Arg Ile Gln Ile Pro Gln Glu Gly Glu Lys Ile Thr<br>1                  5                  10                  15 | | 48 |

```
atg gct tac cag cgc atc cag att ccg cag gag ggc gaa aag atc acc      48
Met Ala Tyr Gln Arg Ile Gln Ile Pro Gln Glu Gly Glu Lys Ile Thr
  1               5                  10                  15 atc caa gag ggc gtc ctg aag gtg ccg gac cag ccc atc atc ggc ttc      96
Ile Gln Glu Gly Val Leu Lys Val Pro Asp Gln Pro Ile Ile Gly Phe
             20                  25                  30 att gag ggg gat ggg acc ggc cct gac atc tgg aga gcg gcc caa ccc     144
Ile Glu Gly Asp Gly Thr Gly Pro Asp Ile Trp Arg Ala Ala Gln Pro
         35                  40                  45 gtc cta gac gcc gcc gtg gcc aaa gcc tac ggc ggg caa cgg cgc atc     192
Val Leu Asp Ala Ala Val Ala Lys Ala Tyr Gly Gly Gln Arg Arg Ile
     50                  55                  60 gtc tgg gtg gag ctt tac gcc ggg gaa aag gcc aac cag gtc tac ggg     240
Val Trp Val Glu Leu Tyr Ala Gly Glu Lys Ala Asn Gln Val Tyr Gly
 65                  70                  75                  80 gag ccc atc tgg ctc ccc gag gag acc ctg gag ttc atc cgg gag tac     288
Glu Pro Ile Trp Leu Pro Glu Glu Thr Leu Glu Phe Ile Arg Glu Tyr
                 85                  90                  95 ctg gtg gcc atc aag ggc ccc ctg acc acg ccg gtg ggc ggc ggc atc     336
Leu Val Ala Ile Lys Gly Pro Leu Thr Thr Pro Val Gly Gly Gly Ile
            100                 105                 110 cgg agc atc aac gtg gcc ctc agg cag gag ctg gac ctc tac gcc tgc     384
Arg Ser Ile Asn Val Ala Leu Arg Gln Glu Leu Asp Leu Tyr Ala Cys
        115                 120                 125 gtg cgc ccc gtg cgc tgg ttc cag ggg gtg ccc agt ccg gtg aag cac     432
Val Arg Pro Val Arg Trp Phe Gln Gly Val Pro Ser Pro Val Lys His
    130                 135                 140 ccg gag ctg gtc aac atg gtc atc ttc cgg gag aac acc gag gac atc     480
Pro Glu Leu Val Asn Met Val Ile Phe Arg Glu Asn Thr Glu Asp Ile
145                 150                 155                 160 tac gcc ggg att gag tgg ccg gcg ggg agc gag gag gta aag aag gtc     528
Tyr Ala Gly Ile Glu Trp Pro Ala Gly Ser Glu Glu Val Lys Lys Val
                165                 170                 175 cta gac ttc ttg aag cgg gag ttc ccc aag gcc tac gcc aag atc cgc     576
Leu Asp Phe Leu Lys Arg Glu Phe Pro Lys Ala Tyr Ala Lys Ile Arg
            180                 185                 190 ttc ccc gag acc tcg ggc ctg ggc ctg aag ccc atc tcc aag gag ggc     624
Phe Pro Glu Thr Ser Gly Leu Gly Leu Lys Pro Ile Ser Lys Glu Gly
        195                 200                 205 acg gag cgc ctg gtg gag gcg gcc att gag tac gcc atc aag gag gac     672
Thr Glu Arg Leu Val Glu Ala Ala Ile Glu Tyr Ala Ile Lys Glu Asp
    210                 215                 220
```

```
ctc ccc agc gtg acc ctg gtc cac aaa ggc aac atc atg aag ttc acc      720
Leu Pro Ser Val Thr Leu Val His Lys Gly Asn Ile Met Lys Phe Thr
225                 230                 235                 240 gaa ggg gcc ttc cgg gag tgg ggc tac gcc ctg gcc cgg gaa aag tac      768
Glu Gly Ala Phe Arg Glu Trp Gly Tyr Ala Leu Ala Arg Glu Lys Tyr
                245                 250                 255 ggg gcc acg ccc ctg gac ggc ggg ccc tgg cac gtc ctc aaa aac ccc      816
Gly Ala Thr Pro Leu Asp Gly Gly Pro Trp His Val Leu Lys Asn Pro
            260                 265                 270 cgc acc ggc agg gag atc gtt atc aag gac atg atc gcc gac aac ttc      864
Arg Thr Gly Arg Glu Ile Val Ile Lys Asp Met Ile Ala Asp Asn Phe
        275                 280                 285 ctg cag cag atc ctc ctc cgc ccc gac gaa tac tcg gtg atc gcc acc      912
Leu Gln Gln Ile Leu Leu Arg Pro Asp Glu Tyr Ser Val Ile Ala Thr
290                 295                 300 atg aac ctg aac ggg gac tac atc tcc gat gcc ctg gcc gcc cag gtg      960
Met Asn Leu Asn Gly Asp Tyr Ile Ser Asp Ala Leu Ala Ala Gln Val
305                 310                 315                 320 ggg ggc atc ggc atc gcc ccc ggg gcc aac atc aac tac aag acg ggc     1008
Gly Gly Ile Gly Ile Ala Pro Gly Ala Asn Ile Asn Tyr Lys Thr Gly
                325                 330                 335 cac gcc gtc ttt gag gcc acc cac ggc acc gcc ccc aag tac gct ggc     1056
His Ala Val Phe Glu Ala Thr His Gly Thr Ala Pro Lys Tyr Ala Gly
            340                 345                 350 cag gac aag gtg aac ccc agc agc gtc atc ctc tcc ggg gag atg atg     1104
Gln Asp Lys Val Asn Pro Ser Ser Val Ile Leu Ser Gly Glu Met Met
        355                 360                 365 ctt cgc tac ctg ggc tgg aac gag gcg gcg gac ctc atc atc agg gcc     1152
Leu Arg Tyr Leu Gly Trp Asn Glu Ala Ala Asp Leu Ile Ile Arg Ala
370                 375                 380 atg gag agg acc atc agc aag ggc ctg gtc acc tac gac ttc cac cgc     1200
Met Glu Arg Thr Ile Ser Lys Gly Leu Val Thr Tyr Asp Phe His Arg
385                 390                 395                 400 ctc ctg gtg gcc gag ggc aag ccc gcc acg ctt ctt aag acc agc gag     1248
Leu Leu Val Ala Glu Gly Lys Pro Ala Thr Leu Leu Lys Thr Ser Glu
                405                 410                 415 ttc ggc cag gcc ctg atc cag cac atg gac tga                         1281
Phe Gly Gln Ala Leu Ile Gln His Met Asp
            420                 425

<210> SEQ ID NO 4
<211> LENGTH: 1284
<212> TYPE: DNA
<213> ORGANISM: Thermus aquaticus
<220> FEATURE:
<221> NAME/KEY: CDS
<222> LOCATION: (1)..(1284)

<400> SEQUENCE: 4 atg gct tac cag cgc atc cag att ccg cag gag ggc gaa aag atc acc       48
Met Ala Tyr Gln Arg Ile Gln Ile Pro Gln Glu Gly Glu Lys Ile Thr
1               5                  10                  15 atc caa gag ggc gtc ctg aag gtg ccg gac cag ccc atc atc ggc ttc       96
Ile Gln Glu Gly Val Leu Lys Val Pro Asp Gln Pro Ile Ile Gly Phe
                20                  25                  30 att gag ggg gat ggg acc ggc cct gac atc tgg aga gcg gcc caa ccc      144
Ile Glu Gly Asp Gly Thr Gly Pro Asp Ile Trp Arg Ala Ala Gln Pro
            35                  40                  45 gtc cta gac gcc gcc gtg gcc aaa gcc tac ggg ggg caa cgg cgc atc      192
Val Leu Asp Ala Ala Val Ala Lys Ala Tyr Gly Gly Gln Arg Arg Ile
        50                  55                  60
```

-continued

| | |
|---|---|
| gtc tgg gtg gag ctt tac gcc ggg gaa aag gcc aac cag gtc tac ggg<br>Val Trp Val Glu Leu Tyr Ala Gly Glu Lys Ala Asn Gln Val Tyr Gly<br>65              70                75              80 | 240 |
| gag ccc atc tgg ctc ccc gag gag acc ctg gag ttc atc cgg gag tac<br>Glu Pro Ile Trp Leu Pro Glu Glu Thr Leu Glu Phe Ile Arg Glu Tyr<br>                85                90                95 | 288 |
| ctg gtg gcc atc aag ggc ccc ctg acc acg ccg gtg ggc ggc ggc atc<br>Leu Val Ala Ile Lys Gly Pro Leu Thr Thr Pro Val Gly Gly Gly Ile<br>100            105              110 | 336 |
| cgg agc atc aac gtg gcc ctc agg cag gag ctg gac ctc tac gcc tgc<br>Arg Ser Ile Asn Val Ala Leu Arg Gln Glu Leu Asp Leu Tyr Ala Cys<br>            115              120              125 | 384 |
| gtg cgc ccc gtg cgc tgg ttc cag ggg gtg ccc agt ccg gtg aag cac<br>Val Arg Pro Val Arg Trp Phe Gln Gly Val Pro Ser Pro Val Lys His<br>130            135              140 | 432 |
| ccg gag ctg gtc aac atg gtc atc ttc cgg gag aac acc gag gac atc<br>Pro Glu Leu Val Asn Met Val Ile Phe Arg Glu Asn Thr Glu Asp Ile<br>145            150              155              160 | 480 |
| tac gcc ggg att gag tgg ccg gcg ggc agc gag gag gta aag aag gtc<br>Tyr Ala Gly Ile Glu Trp Pro Ala Gly Ser Glu Glu Val Lys Lys Val<br>                165              170              175 | 528 |
| cta gac ttc ttg aag cgg gag ttc ccc aag gcc tac gcc aag atc cgc<br>Leu Asp Phe Leu Lys Arg Glu Phe Pro Lys Ala Tyr Ala Lys Ile Arg<br>            180              185              190 | 576 |
| ttc ccc gag acc tcg ggc ctg ggc ctg aag ccc atc tcc aag gag ggc<br>Phe Pro Glu Thr Ser Gly Leu Gly Leu Lys Pro Ile Ser Lys Glu Gly<br>              195              200              205 | 624 |
| acg gag cgc ctg gtg gag gcg gcc att gag tac gcc atc aag gag gac<br>Thr Glu Arg Leu Val Glu Ala Ala Ile Glu Tyr Ala Ile Lys Glu Asp<br>210            215              220 | 672 |
| ctc ccc agc gtg acc ctg gtc cac aaa ggc aac atc atg aag ttc acc<br>Leu Pro Ser Val Thr Leu Val His Lys Gly Asn Ile Met Lys Phe Thr<br>225            230              235              240 | 720 |
| gaa ggg gcc ttc cgg gag tgg ggc tac gcc ctg gcc cgg gaa aag tac<br>Glu Gly Ala Phe Arg Glu Trp Gly Tyr Ala Leu Ala Arg Glu Lys Tyr<br>              245              250              255 | 768 |
| ggg gcc acg ccc ctg gac ggc ggg ccc tgg cac gtc ctc aaa aac ccc<br>Gly Ala Thr Pro Leu Asp Gly Gly Pro Trp His Val Leu Lys Asn Pro<br>260            265              270 | 816 |
| cgc acc ggc agg gag atc gtt atc aag gac atg atc gcc gac aac ttc<br>Arg Thr Gly Arg Glu Ile Val Ile Lys Asp Met Ile Ala Asp Asn Phe<br>275            280              285 | 864 |
| ctg cag cag atc ctc ctc cgc ccc gac gaa tac tcg gtg atc gcc acc<br>Leu Gln Gln Ile Leu Leu Arg Pro Asp Glu Tyr Ser Val Ile Ala Thr<br>290            295              300 | 912 |
| atg aac ctg aac ggg gac tac atc tcc gat gcc ctg gcc gcc cag gtg<br>Met Asn Leu Asn Gly Asp Tyr Ile Ser Asp Ala Leu Ala Ala Gln Val<br>305            310              315              320 | 960 |
| ggg ggc atc ggc atc gcc ccc ggg gcc aac atc aac tac aag acg ggc<br>Gly Gly Ile Gly Ile Ala Pro Gly Ala Asn Ile Asn Tyr Lys Thr Gly<br>              325              330              335 | 1008 |
| cac gcc gtc ttt gag gcc acc cac ggc acc gcc ccc aag tac gct ggc<br>His Ala Val Phe Glu Ala Thr His Gly Thr Ala Pro Lys Tyr Ala Gly<br>            340              345              350 | 1056 |
| cag gac aag gtg aac ccc agc agc gtc atc ctc tcc ggg gag atg atg<br>Gln Asp Lys Val Asn Pro Ser Ser Val Ile Leu Ser Gly Glu Met Met<br>            355              360              365 | 1104 |
| ctt cgc tac ctg ggc tgg aac gag gcg gcg gac ctc atc atc agg gcc<br>Leu Arg Tyr Leu Gly Trp Asn Glu Ala Ala Asp Leu Ile Ile Arg Ala<br>370            375              380 | 1152 |

| | | | | | | | | | | | | |
|---|---|---|---|---|---|---|---|---|---|---|---|---|
| atg | gag | agg | acc | atc | agc | aag | ggc | ctg | gtc | acc | tac | gac | ttc | cac | cgc | 1200 |
| Met | Glu | Arg | Thr | Ile | Ser | Lys | Gly | Leu | Val | Thr | Tyr | Asp | Phe | His | Arg | |
| 385 | | | | 390 | | | | | 395 | | | | | 400 | | |
| ctc | ctg | gtg | gcc | gag | ggc | aag | ccc | gcc | acg | ctt | ctt | aag | acc | agc | gag | 1248 |
| Leu | Leu | Val | Ala | Glu | Gly | Lys | Pro | Ala | Thr | Leu | Leu | Lys | Thr | Ser | Glu | |
| | | | | 405 | | | | | 410 | | | | | 415 | | |
| ttc | ggc | cag | gcc | ctg | atc | cag | cac | atg | gac | taa | tga | | | | | 1284 |
| Phe | Gly | Gln | Ala | Leu | Ile | Gln | His | Met | Asp | | | | | | | |
| | | | | 420 | | | | 425 | | | | | | | | |

<210> SEQ ID NO 5
<211> LENGTH: 426
<212> TYPE: PRT
<213> ORGANISM: Thermus aquaticus

<400> SEQUENCE: 5

Met Ala Tyr Gln Arg Ile Gln Ile Pro Gln Glu Gly Glu Lys Ile Thr
 1               5                  10                  15

Ile Gln Glu Gly Val Leu Lys Val Pro Asp Gln Pro Ile Ile Gly Phe
             20                  25                  30

Ile Glu Gly Asp Gly Thr Gly Pro Asp Ile Trp Arg Ala Ala Gln Pro
         35                  40                  45

Val Leu Asp Ala Val Ala Lys Ala Tyr Gly Gly Gln Arg Arg Ile
     50                  55                  60

Val Trp Val Glu Leu Tyr Ala Gly Glu Lys Ala Asn Gln Val Tyr Gly
 65                  70                  75                  80

Glu Pro Ile Trp Leu Pro Glu Thr Leu Glu Phe Ile Arg Glu Tyr
                 85                  90                  95

Leu Val Ala Ile Lys Gly Pro Leu Thr Thr Pro Val Gly Gly Gly Ile
             100                 105                 110

Arg Ser Ile Asn Val Ala Leu Arg Gln Glu Leu Asp Leu Tyr Ala Cys
         115                 120                 125

Val Arg Pro Val Arg Trp Phe Gln Gly Val Pro Ser Pro Val Lys His
     130                 135                 140

Pro Glu Leu Val Asn Met Val Ile Phe Arg Glu Asn Thr Glu Asp Ile
145                 150                 155                 160

Tyr Ala Gly Ile Glu Trp Pro Ala Gly Ser Glu Glu Val Lys Lys Val
                 165                 170                 175

Leu Asp Phe Leu Lys Arg Glu Phe Pro Lys Ala Tyr Ala Lys Ile Arg
             180                 185                 190

Phe Pro Glu Thr Ser Gly Leu Gly Leu Lys Pro Ile Ser Lys Glu Gly
         195                 200                 205

Thr Glu Arg Leu Val Glu Ala Ala Ile Glu Tyr Ala Ile Lys Glu Asp
     210                 215                 220

Leu Pro Ser Val Thr Leu Val His Lys Gly Asn Ile Met Lys Phe Thr
225                 230                 235                 240

Glu Gly Ala Phe Arg Glu Trp Gly Tyr Ala Leu Ala Arg Glu Lys Tyr
                 245                 250                 255

Gly Ala Thr Pro Leu Glu Gly Gly Pro Trp His Val Leu Lys Asn Pro
             260                 265                 270

Arg Thr Gly Arg Glu Ile Val Ile Lys Asp Met Ile Ala Asp Asn Phe
         275                 280                 285

Leu Gln Gln Ile Leu Leu Arg Pro Asp Glu Tyr Ser Val Ile Ala Thr
     290                 295                 300

Met Asn Leu Asn Gly Asp Tyr Ile Ser Asp Ala Leu Ala Ala Gln Val
305                 310                 315                 320

```
Gly Gly Ile Gly Ile Ala Pro Gly Ala Asn Ile Asn Tyr Lys Thr Gly
                325                 330                 335

His Ala Val Phe Glu Ala Thr His Gly Thr Ala Pro Lys Tyr Ala Gly
                340                 345                 350

Gln Asp Lys Val Asn Pro Ser Ser Val Ile Leu Ser Gly Glu Met Met
                355                 360                 365

Leu Arg Tyr Leu Gly Trp Asn Glu Ala Ala Asp Leu Ile Ile Arg Ala
                370                 375                 380

Met Glu Arg Thr Ile Ser Lys Gly Leu Val Thr Tyr Asp Phe His Arg
385                 390                 395                 400

Leu Leu Val Ala Glu Gly Lys Pro Ala Thr Leu Leu Lys Thr Ser Glu
                405                 410                 415

Phe Gly Gln Ala Leu Ile Gln His Met Asp
                420                 425

<210> SEQ ID NO 6
<211> LENGTH: 426
<212> TYPE: PRT
<213> ORGANISM: Thermus aquaticus

<400> SEQUENCE: 6

Met Ala Tyr Gln Arg Ile Gln Ile Pro Gln Glu Gly Glu Lys Ile Thr
1               5                   10                  15

Ile Gln Glu Gly Val Leu Lys Val Pro Asp Gln Pro Ile Ile Gly Phe
                20                  25                  30

Ile Glu Gly Asp Gly Thr Gly Pro Asp Ile Trp Arg Ala Ala Gln Pro
                35                  40                  45

Val Leu Asp Ala Val Ala Lys Ala Tyr Gly Gly Gln Arg Arg Ile
                50              55                  60

Val Trp Val Glu Leu Tyr Ala Gly Glu Lys Ala Asn Gln Val Tyr Gly
65                  70                  75                  80

Glu Pro Ile Trp Leu Pro Glu Glu Thr Leu Glu Phe Ile Arg Glu Tyr
                85                  90                  95

Leu Val Ala Ile Lys Gly Pro Leu Thr Thr Pro Val Gly Gly Gly Ile
                100                 105                 110

Arg Ser Ile Asn Val Ala Leu Arg Gln Glu Leu Asp Leu Tyr Ala Cys
                115                 120                 125

Val Arg Pro Val Arg Trp Phe Gln Gly Val Pro Ser Pro Val Lys His
130                 135                 140

Pro Glu Leu Val Asn Met Val Ile Phe Arg Glu Asn Thr Glu Asp Ile
145                 150                 155                 160

Tyr Ala Gly Ile Glu Trp Pro Ala Gly Ser Glu Glu Val Lys Lys Val
                165                 170                 175

Leu Asp Phe Leu Lys Arg Glu Phe Pro Lys Ala Tyr Ala Lys Ile Arg
                180                 185                 190

Phe Pro Glu Thr Ser Gly Leu Gly Leu Lys Pro Ile Ser Lys Glu Gly
                195                 200                 205

Thr Glu Arg Leu Val Glu Ala Ala Ile Glu Tyr Ala Ile Lys Glu Asp
                210                 215                 220

Leu Pro Ser Val Thr Leu Val His Lys Gly Asn Ile Met Lys Phe Thr
225                 230                 235                 240

Glu Gly Ala Phe Arg Glu Trp Gly Tyr Ala Leu Ala Arg Glu Lys Tyr
                245                 250                 255

Gly Ala Thr Pro Leu Asp Gly Gly Pro Trp His Val Leu Lys Asn Pro
                260                 265                 270
```

```
Arg Thr Gly Arg Glu Ile Val Ile Lys Asp Met Ile Ala Asp Asn Phe
            275                 280                 285

Leu Gln Gln Ile Leu Leu Arg Pro Asp Glu Tyr Ser Val Ile Ala Thr
        290                 295                 300

Met Asn Leu Asn Gly Asp Tyr Ile Ser Asp Ala Leu Ala Ala Gln Val
305                 310                 315                 320

Gly Gly Ile Gly Ile Ala Pro Gly Ala Asn Ile Asn Tyr Lys Thr Gly
                325                 330                 335

His Ala Val Phe Glu Ala Thr His Gly Thr Ala Pro Lys Tyr Ala Gly
            340                 345                 350

Gln Asp Lys Val Asn Pro Ser Ser Val Ile Leu Ser Gly Glu Met Met
        355                 360                 365

Leu Arg Tyr Leu Gly Trp Asn Glu Ala Ala Asp Leu Ile Ile Arg Ala
    370                 375                 380

Met Glu Arg Thr Ile Ser Lys Gly Leu Val Thr Tyr Asp Phe His Arg
385                 390                 395                 400

Leu Leu Val Ala Glu Gly Lys Pro Ala Thr Leu Leu Lys Thr Ser Glu
                405                 410                 415

Phe Gly Gln Ala Leu Ile Gln His Met Asp
            420                 425

<210> SEQ ID NO 7
<211> LENGTH: 426
<212> TYPE: PRT
<213> ORGANISM: Thermus aquaticus

<400> SEQUENCE: 7

Met Ala Tyr Gln Arg Ile Gln Ile Pro Gln Glu Gly Glu Lys Ile Thr
1               5                   10                  15

Ile Gln Glu Gly Val Leu Lys Val Pro Asp Gln Pro Ile Ile Gly Phe
            20                  25                  30

Ile Glu Gly Asp Gly Thr Gly Pro Asp Ile Trp Arg Ala Ala Gln Pro
        35                  40                  45

Val Leu Asp Ala Ala Val Ala Lys Ala Tyr Gly Gly Gln Arg Arg Ile
    50                  55                  60

Val Trp Val Glu Leu Tyr Ala Gly Glu Lys Ala Asn Gln Val Tyr Gly
65                  70                  75                  80

Glu Pro Ile Trp Leu Pro Glu Glu Thr Leu Glu Phe Ile Arg Glu Tyr
                85                  90                  95

Leu Val Ala Ile Lys Gly Pro Leu Thr Thr Pro Val Gly Gly Gly Ile
            100                 105                 110

Arg Ser Ile Asn Val Ala Leu Arg Gln Glu Leu Asp Leu Tyr Ala Cys
        115                 120                 125

Val Arg Pro Val Arg Trp Phe Gln Gly Val Pro Ser Pro Val Lys His
    130                 135                 140

Pro Glu Leu Val Asn Met Val Ile Phe Arg Glu Asn Thr Glu Asp Ile
145                 150                 155                 160

Tyr Ala Gly Ile Glu Trp Pro Ala Gly Ser Glu Val Lys Lys Val
                165                 170                 175

Leu Asp Phe Leu Lys Arg Glu Phe Pro Lys Ala Tyr Ala Lys Ile Arg
            180                 185                 190

Phe Pro Glu Thr Ser Gly Leu Gly Leu Lys Pro Ile Ser Lys Glu Gly
        195                 200                 205

Thr Glu Arg Leu Val Glu Ala Ala Ile Glu Tyr Ala Ile Lys Glu Asp
    210                 215                 220
```

-continued

```
Leu Pro Ser Val Thr Leu Val His Lys Gly Asn Ile Met Lys Phe Thr
225                 230              235                 240

Glu Gly Ala Phe Arg Glu Trp Gly Tyr Ala Leu Ala Arg Glu Lys Tyr
            245              250                 255

Gly Ala Thr Pro Leu Asp Gly Gly Pro Trp His Val Leu Lys Asn Pro
            260              265                 270

Arg Thr Gly Arg Glu Ile Val Ile Lys Asp Met Ile Ala Asp Asn Phe
        275              280              285

Leu Gln Gln Ile Leu Leu Arg Pro Asp Glu Tyr Ser Val Ile Ala Thr
    290              295              300

Met Asn Leu Asn Gly Asp Tyr Ile Ser Asp Ala Leu Ala Ala Gln Val
305             310              315                 320

Gly Gly Ile Gly Ile Ala Pro Gly Ala Asn Ile Asn Tyr Lys Thr Gly
                325              330              335

His Ala Val Phe Glu Ala Thr His Gly Thr Ala Pro Lys Tyr Ala Gly
            340              345              350

Gln Asp Lys Val Asn Pro Ser Ser Val Ile Leu Ser Gly Glu Met Met
            355              360              365

Leu Arg Tyr Leu Gly Trp Asn Glu Ala Ala Asp Leu Ile Ile Arg Ala
    370              375              380

Met Glu Arg Thr Ile Ser Lys Gly Leu Val Thr Tyr Asp Phe His Arg
385             390              395              400

Leu Leu Val Ala Glu Gly Lys Pro Ala Thr Leu Leu Lys Thr Ser Glu
            405              410              415

Phe Gly Gln Ala Leu Ile Gln His Met Asp
            420              425
```

AMMONIA ELIMINATION LIQUID REAGENT

DETAILED DESCRIPTION OF THE INVENTION

1. Technical Field to Which the Invention Belongs

The present invention relates to an assay method of a biological substance generating a reaction product ammonia in a sample in an accurate manner, comprising preliminarily allowing ammonia present in the sample to be consumed up; and the invention also relates to an ammonia elimination liquid reagent for the assay method, wherein use is made of a thermo-resistant isocitrate dehydrogenase with excellent stability at alkaline pHs suitable for the ammonia elimination liquid reagent as a conjugative enzyme.

2. Prior Art

Generally, detection of urea, creatinine, creatine, guanine and adenosine and the like in biological samples such as urine and serum, as well as assay of the activities of various enzymes relevant to these substances, is routinely conducted. For the detection of these substances and during reactions with the enzyme, ammonia once generated is converted to glutamic acid via glutamate dehydrogenase (sometimes abbreviated as GLD hereinbelow), to assay the NADPH decrease through the conjugation reaction: reduced nicotineamide adenine dinucleotide phosphate (NADPH) →nicotineamide adenine dinucleotide phosphate ($NADP^+$). The assay was conducted at 340 nm.

In the reaction system, ammonia is assayed as a reaction product, so ammonia primarily present in a sample is also assayed and included in the resulting assay value. Therefore, these biological substances have hardly been accurately assayed. Hence, ammonia present ina sample is allowed to react with 2-oxoglutaric acid via GLD at a preliminary process, so that the ammonia is converted to glutamic acid; the reaction system for the conversion of ammonia to glutamic acid involves the change $NAD(P)H \rightarrow NAD(P)^+$, so the reverse reaction $NAD(P)^+ \rightarrow NAD(P)H$ is needed to resume NAD(P)H. In this case, a conjugative reaction can be induced, with a substrate isocitric acid, isocitrate dehydrogenase and a metal ion such as magnesium ion or manganese ion. The reaction scheme is shown in FIG. 1.

The present inventors have invented a liquid ammonia elimination reagent for the elimination of such ammonia and have submitted the patent application thereof (JP-A-9-295). A thermo-resistant isocitrate dehydrogenase derived from genus Sulfolobus is used in the ammonia elimination reagent designed by the inventors. With the enzyme, however, high-level endogenous ammonia cannot thoroughly be eliminated within a given period of time (a reaction time of about 5 minutes for automatic analyzers), when a biological substance generating ammonia as a product, for example urea nitrogen, is to be assayed directly in a sample of intact urine with no dilution. Additionally, the enzyme should be used for conventional enzyme systems, namely enzyme systems essentially requiring NADPH as a reduced coenzyme, so the enzyme is disadvantageous economically and in terms of solution stability. Hence, the enzyme is not yet sufficiently satisfactory.

PROBLEMS THAT THE INVENTION IS TO SOLVE

In recent years, a great number of laboratory test reagents in freeze-dried powers are likely to be replaced with those in solutions. The reason is that the procedure for dissolving powdery reagents in solutions prior to each use can thereby be skipped, leading to great reduction of such burdensome works on sites.

From the standpoints of higher stability in solution under storage and cost, it is needed to use NADH in place of a reduced coenzyme NADPH having been used in conventional ammonia elimination liquid reagents. However, many of isocitrate dehydrogenase species have been in combination uniquely with NADPH, so NADH has never successfully been used therefor. In other words, isocitrate dehydrogenase species of NADP+ type have essentially been used for conventional NADPH- type systems, using for example GLD.

As has been described above, conventional ammonia elimination liquid reagents are mostly in combination with NADPH, because the use of NADH therefor is absolutely never possible. It has been known a unique yeast-derived isocitrate dehydrogenase of $NAD^+$ type. Because the enzyme is extracted from yeast only through various instrumental processes, the enzyme is hardly available at low cost; additionally, the enzyme can never satisfactorily be kept under storage in a solution state, so the enzyme can never be used for NADPH-type systems.

In such technical circumstances, the inventors have attempted to develop a novel ammonia elimination liquid reagent using a thermo-resistant isocitrate dehydrogenase, with responsiveness to NAD and responsiveness to NADP whereby the reagent can be incorporated into conventional systems and with long-term storability at alkaline pHs.

MEANS FOR SOLVING THE PROBLEMS

Figure 1:
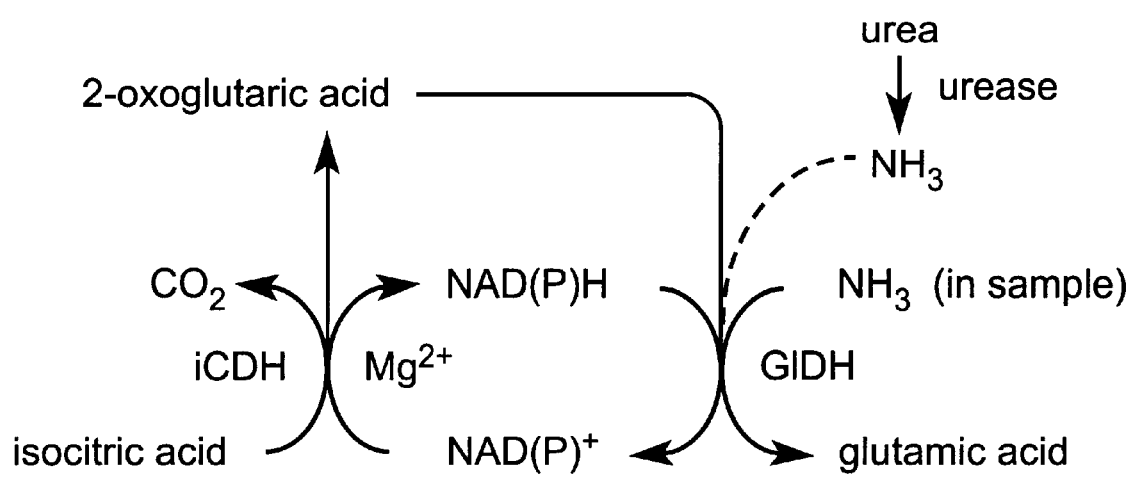
FIG. 1 depicts the reaction scheme for ammonia elimination.

The inventors have made investigations about isocitrate dehydrogenase in view of the conventional problems. Consequently, the inventors have found that an isocitrate dehydrogenase (represented sometimes as ICD or ICDH hereinafter) derived from highly thermophilic bacteria of the genus Thermus is a thermo-resistant enzyme and is highly stable under alkaline conditions.

The inventors have subsequently found that the inventive thermo-resistant ICDH from the genus Thermus can eliminate a higher concentration of endogenous ammonia during a short-term reaction according to the ammonia elimination method than when the thermo-resistant ICDH from the genus Sulfolobus is used. When biological substances generating ammonia, for example urea nitrogen, are to be assayed in biological samples with a high concentration of ammonia present therein, for example intact urine, consequently, the urea nitrogen in an intact urine sample can be assayed with no preliminary dilution of the intact urine sample, so the preliminary reaction can be terminated for a given period of time.

For the designing of a stable ammonia elimination liquid reagent, it is critical to use a reduced enzyme NADH with greater stability in solution. The inventors have first found a novel isocitrate dehydrogenase with substantial responsiveness to both the coenzymes $NADP^+$ and $NAD^+$ and that an ammonia elimination liquid reagent stable for a longer term can be composed of a combination of the isocitrate dehydrogenase and NADH. Thus, the invention has been achieved.

The invention relates to an ammonia elimination liquid reagent of a reagent composition comprising a reduced coenzyme NAD(P)H, glutamate dehydrogenase, substrates and the thermo-resistant isocitrate dehydrogenase with responsiveness to both $NADP^+$ and $NAD^+$, wherein the ammonia elimination liquid reagent is stable under conditions at alkaline pHs for a long term. The invention additionally relates to an assay method of a biological substance generating ammonia by using the ammonia elimination liquid reagent, comprising allowing ammonia present in a sample to be consumed up, adding then a chelating agent to the sample to terminate the isocitrate dehydrogenase reaction, and simultaneously or thereafter adding an enzyme capable of generating ammonia as a reaction product with the biological substance, to assay the generated ammonia.

As the isocitrate dehydrogenase for use in accordance with the invention, any of isocitrate dehydrogenase species with responsiveness to both $NADP^+$ and $NAD^+$ and great stability at alkaline pHs and with thermal resistance may satisfactorily be used.

Non-limiting examples thereof are thermo-resistant isocitrate dehydrogenase species derived from acid-fast and thermophilic Thermus species, for example a *Thermus thermophilus* strain HB8 (ATCC 27634) and a *Thermus aquaticus* strain YT1 (ATCC 25104), as well as synthetic isocitrate dehydrogenase species.

More specifically, the objective enzyme described below can be prepared, by culturing a *Thermus thermophilus* strain HB8 (ATCC 27634), collecting the culture, particularly the bacteria, subjecting the supernatant of the bacterial culture to ammonium sulfate fractionation (removing nucleic acids if necessary), and purifying an enzyme-containing fraction by an appropriate combination of general enzyme purification means. Novel thermo-resistant isocitrate dehydrogenase with the following physico-chemical properties.

(a) Thermal resistance
  Even after the enzyme is left to stand at 90° C. for 15 minutes, 40% or more of the activity of the enzyme can be retained.
(b) Coenzyme utilization
  The enzyme utilizes both the coenzymes NAD and NADP.
(c) Chemical resistance against modifying agents
  The enzyme retains 70% or more of the activity in 2 M urea.
(d) Molecular weight
  By high-performance liquid chromatography, the enzyme shows a sharp peak at a position of a molecular weight of 85,000.

In the same manner, the objective thermo-resistant isocitrate dehydrogenase can be recovered by culturing a Thermus species, for example a *Thermus aquaticus* strain YT1 (ATCC 25104) and extracting the thermo-resistant isocitrate dehydrogenase from the culture and purifying the thermo-resistant isocitrate dehydrogenase. One example is the thermo-resistant isocitrate dehydrogenase represented by the amino acid sequence of SQ ID No. 1 in the Sequence Listing. The enzyme can be recovered by such culturing as described above and can additionally be recovered by synthesis based on the identified amino acid sequence.

As described above, the thermo-resistant isocitrate dehydrogenase for use in accordance with the invention can be recovered by mean of extraction of the enzyme from the bacteria of a Thermus species and subsequent purification of the enzyme or is satisfactorily a recombinant thermo-resistant isocitrate dehydrogenase generated by a transformed bacterial strain prepared by inserting a DNA vector with the gene information of the thermo-resistant isocitrate dehydrogenase derived from the genus Thermus into a certain host bacterial strain. Bacterial species including for example *Escherichia coli* (sometimes abbreviated as *E. coli*), yeast, Actinomyces, and *Bacillus subtilus* are used as the host bacteria therefor. According to the disclosure of the present Specification, a person skilled in the art can readily recover a thermo-resistant isocitrate dehydrogenase with responsiveness to both $NADP^+$ and $NAD^+$. For example, a recombinant thermo-resistant isocitrate dehydrogenase is disclosed in the prior application JP8-328400 (JP-A-10-165181) entitled thermo-resistant isocitrate dehydrogenase gene, the application having been submitted also by the present inventors.

The inventors have successfully attained the cloning of the thermo-resistant isocitrate dehydrogenase gene from the chromosomal DNA of the *Thermus aquaticus* strain YT1 (ATCC 25104). Furthermore, the inventors have determined the nucleotide sequence with success. The amino acid sequence of the thermo-resistant isocitrate dehydrogenase and the nucleotide sequence of the DNA of the thermo-resistant isocitrate dehydrogenase (ICD) gene are individually shown as SQ ID Nos. 1 and 2, respectively.

*Escherichia coli* was transformed by using a high expression plasmid pEXAC1 prepared by inserting the thermo-resistant ICD. into a vector. The resulting transformant was deposited as FERM P-15962 on Nov. 28, 1996 and transferred therefrom to deposit under Budapest Treaty as FERM BP-6704 on Apr. 16, 1999 in National Institute of Bioscience and Human-Technology, Agency of Industrial Science and Technology of 1–3, Higashi 1 chome, Tsukuba-shi, Ibaraki-ken, Japan.

The thermo-resistant ICD recovered by culturing and allowing the transformant (FERM BP-6704) to express the gene and extracting the resulting enzyme from the culture, particularly the bacteria, is used in accordance with the invention.

For example, the transformant is cultured in a liquid culture medium, pH 7.5, supplemented with 1.6% tryptone, 1.0% yeast extract, 0.5% NaCl, 0.1 mM IPTG, and 100 $\mu/\mu l$ ampicillin, at 37° C. overnight under agitation, followed by centrifugation at 4,000 rpm for 10 minutes. The harvested bacteria are suspended in a 3-fold-volume solution containing 10 mM Tris HCl, pH 7.6 and 0.5 mM EDTA and are then disrupted therein under ultrasonication.

The suspension is ultra-centrifuged at 45,000 rpm for 30 minutes; the resulting supernatant of the cell extract is transferred into another tube for heating treatment at 70° C. for 30 minutes; by subsequently removing the deposited denatured protein by centrifugation, the resulting supernatant is purified by using DEAE TOYO Pearl (product manufactured by TOSO, Co., Ltd.).

The recombinant thermo-resistant ICD thus recovered has the following properties:

(1) optimum temperature around 85° C.;
(2) optimum pH around 8 to 9.5;
(3) thermal resistance with no loss of the initial activity even after heating treatment at 80° C. for 10 minutes and with an activity about 2/3-fold the initial activity, after heating treatment at 90° C.; and
(4) responsiveness with both $NADP^+$ and $NAD^+$.

The Km values of the thermo-resistant ICD for $NADP^+$ and $NAD^+$ are 20 $\mu$M and 1 mM, respectively; the Km values of the thermo-resistant ICD from the genus Thermus as disclosed in JP 2639803 (JP-A-63-214182) for $NADP^+$ and $NAD^+$ are 20 $\mu$M and 2.6 mM, respectively, alike. It is found by the inventors that the Km value of any of the enzymes for $NAD^+$ is small, so that the inventive thermo-resistant ICD can compose an ammonia elimination system using any of $NADP^+$ and $NAD^+$, although the conventional ICD can never eliminate ammonia using $NAD^+$. The novel finding has first been applied to an ammonia elimination liquid reagent, with success.

Still furthermore, focusing their attention to industrial application thereof after the success, the inventors have made investigations about the mass-scale production of the thermo-resistant ICD and have successfully developed a method for the production.

More specifically, the method previously developed by the inventors is excellent, as no such method has existed conventionally. Nevertheless, the method has the following drawbacks; the production cost per unit volume of bacterial culture is high because of the induction expression using chemical agents (IPTG as an abbreviation of isopropyl β-D-galactopyranoside); culture productivity is low due to the low content of the enzyme per unit wet weight of bacteria; for expression and accumulation of a recombinant thermo-resistant isocitrate dehydrogenase through chemical induction, a transformant can be recovered only by batch culture, so it is difficult to improve the productivity per unit culture by the increase of a collected bacterial volume per culture. Accordingly, the method can never provide an economical recombinant thermo-resistant isocitrate dehydrogenase by a mass-scale production. Thus, the method is not sufficiently satisfactory.

In the state of the art, the invention has been achieved for the purpose of developing a system to produce an isocitrate dehydrogenase by a more economical high-density culture method, practical at an industrial scale, wherein the isocitrate dehydrogenase is expressed intracellularly in a designed *Escherichia coli* expression system with no use of the chemical agents.

Meanwhile, the inventors have made intensive examinations on the nucleotide substitution of the nucleotide sequence of SQ ID No. 2 with no change in the amino acid sequence of the thermo-resistant ICD. As a result, totally unexpectedly, the inventors have first found that the second codon GCC (GCC specifying alanine, at positions 183 to 185 in the nucleotide sequence of SQ ID No. 2) from the translation initiation codon ATG in the thermo-resistant ICD gene of a sequence length of 2872 and the ninth codon CCC (CCC specifying proline, at positions 204 to 206 therein) from the same ATG are highly responsible for the mass expression and mass generation of thermo-resistant ICD.

By further investigations subsequent to the finding, the inventors have attempted to substitute the second codon GCC and/or the ninth codon CCC with other nucleotides, resulting in a high expression ratio of the enzyme with no need of chemical (IPTG) induction expression, so that a continuous fed batch culture method could be adopted for the first time for the enzyme with no need of batch culture, which consequently brings about the increase of the collected bacterial transformant in volume, leading to the production of a greater amount of ICD.

The invention has thus been achieved on the basis of these useful findings. Successfully, genes carrying the isocitrate dehydrogenase gene sequence not only can be designed but also can be prepared in a practical sense. Additionally, various skillful techniques in terms of the genetic recombination technology have been employed therefor, so that the genes can be expressed efficiently with success.

The invention is now described more specifically below.

The DNA (of the nucleotide sequence of SQ ID No. 2) of the gene encoding the thermo-resistant ICD (of the amino acid sequence of SQ ID No. 1) derived from *Thermus aquaticus* can be recovered from a transformant (FERM BP-6704) prepared by transforming an *Escherichia coli* strain by using for example a thermo-resistant ICD high expression plasmid pEXAC1 or may satisfactorily be synthetically produced by PCR or others, on the basis of SQ ID No. 2.

So as to practice the invention, a sequence of the gene encoding thermo-resistant ICD is designed, on the basis of the novel findings for the efficient expression thereof in *E. coli*.

More specifically, a gene sequence of thermo-resistant isocitrate dehydrogenase was designed, using a primer wherein the second codon GCC and the ninth codon CCC from the translation initiation codon ATG in the structural gene in the nucleotide sequence of SQ ID No. 2 were substituted with GCT, GCA or GCG and CCT, CCA or CCG, respectively and wherein a part of the structural gene is substituted with optimum codons for *E. coli*.

Additionally, restriction sites (for EcoRI and BamHI) are conjugated to both the ends for the purpose of cloning. The resulting primer is integrated in an expression vector (for example, pTRP vector), to transform an *E. coli* strain JM109 (manufactured by TAKARA, Co., Ltd.). By culturing the resulting transformed bacterial *E. coli* strain by high-density culturing by a continuous fed batch culture method using assimilable sugar sources and vitamins and nitrogen sources such as amino acids and/or using as a control dissolved oxygen concentration, a transformant expressing a high level of a recombinant thermo-resistant ICD can be recovered.

Then, the transformant is disrupted, to recover thermo-resistant ICD generated in the cytoplasms as follows.

More specifically, by harvesting the bacteria by filtration or centrifugation of the culture, disrupting the bacteria by a mechanical means or an enzymatic means with lysozyme, and adding then a chelating agent such as ethylenediaminetetraacetic acid (EDTA) and/or a surfactant to the resulting bacterial matter to solubilize thermo-resistant isocitrate dehydrogenase, the isocitrate dehydrogenase is isolated and recovered in the form of an aqueous solution.

The solution of the thermo-resistant isocitrate dehydrogenase thus recovered is subjected to for example concentration under reduced pressure or membrane concentration, and then to salting-out treatment with ammonium sulfate and sodium sulfate or fractionation and precipitation with hydrophilic organic solvents, for example methanol, ethanol and acetone, to precipitate the thermo-resistant isocitrate dehydrogenase.

In accordance with the invention, characteristically, an ammonia elimination liquid reagent can be composed of the specific thermo-resistant ICD and additionally of 2-oxoglutaric acid (α-ketoglutaric acid), reduced coenzymes, isocitric acid, glutamate dehydrogenase, and a metal ion (magnesium ion, manganese ion, etc.).

In accordance with the invention, the reduced coenzymes include NADH, NADPH, and ATP and derivatives of these reduced coenzymes such as thio-NADH (reduced thio-nicotineamide adenine dinucleotide), thio-NADPH (reduced thio-nicotineamide adenine dinucleotide phosphate), APADPH (reduced acetylpyridine adenine dinucleotide phosphate), and the like.

In accordance with the invention, the thermo-resistant ICD responsive to both $NADP^+$ and $NAD^+$ can be used, whereby the use of costly advantageous NADH is attained, together with the use of NADPH for the conventional systems. Owing to the thermo-resistant ICD, characteristically, kits are readily designed.

For preparing an ammonia elimination liquid reagent stable in solution, a buffer with a buffering action at an alkaline pH around 8 to 11, preferably around pH 9 to 11, is selectively used for the stability of a reduced coenzyme in solution.

Various buffers optimum for the ICD are described in the catalog of Dojin Chemical Research Institute (20th edition, 1996), preferably including buffers, for example triethanolamine, TAPS (N-tris(hydroxymethyl)methyl-3-aminopropanesulfonic acid), CHES (N-cyclohexyl-2-aminoethanesulfonic acid), CAPSO (N-cyclohexyl-2-hydroxy-3-aminopropanesulfonic acid), and CAPS (N-cyclohexyl-3-aminopropanesulfonic acid).

An ammonia elimination liquid reagent of any of the following compositions shown in the list of reagent compositions can be prepared, by using the inventive isocitrate dehydrogenase from the genus Thermus. Any buffer with a buffering action at alkaline pHs may satisfactorily be used for preparing the ammonia elimination liquid reagent. In the list, one unit of GLD is defined as the quantity with an activity capable of generating 1 μmol $NADP^+$ per one minute. If necessary, surfactants such as Briji-35 may be added to the reagent.

| Ammonia elimination liquid reagent composition. (composition example) | |
| --- | --- |
| 2-Oxoglutaric acid | 6.4 mM |
| NADPH | 0.3 mM |
| Potassium isocitrate | 10 mM |
| GLD | 20–100 U/ml |
| ICDH | 1–10 U/ml |
| $MgCl_2$ | 0.2 mM |
| pH | 9–10 (preferably, 9.5) |

For preparing an ammonia elimination liquid reagent, the other principal component GLD includes those derived from yeast, genera Proteus and Bacillus. For preparing an ammonia elimination liquid reagent, particularly, any GLD with great stability and with a high activity to generate glutamic acid at alkaline pHs, may be satisfactory.

The method for assaying the activity of isocitrate dehydrogenase is carried out as described below, unless otherwise stated.

Assay temperature: 37° C.
Reaction solution: 0.1 M Tris-HCl buffer, pH 8.5;
  5.0 mM Potassium isocitrate;
  1.0 mM $NADP^+$; and
  5.0 mM $MgCl_2$.
Assay apparatus: spectrophotometer of type U-2000 manufactured by Hitachi, Co., Ltd.
Calculation of enzyme activity:
  Based on the change of the absorbance at 340 nm per one minute, the enzyme activity was assayed spectrophotometrically; and one unit (1 U) of ICD was defined as the quantity with an activity to generate 1 μmol NADPH per one minute.

MODE FOR CARRYING OUT THE INVENTION

The invention is now described in examples.

EXAMPLE 1

Thermo-resistant isocitrate dehydrogenase was purified from *Thermus aguaticus* as follows.

A recombinant isocitrate dehydrogenase was prepared as described in APPL. ENVIRON. MICROBIOL., Vol. 62, No. 12, 4627–31 (1996). By culturing at 37° C. an *Escherichia coli* transformant (FERM BP-6704) with *Thermus aquaticus*-derived thermo-resistant isocitrate dehydrogenase gene inserted therein, a recombinant thermo-resistant dehydrogenase was recovered and purified from the bacterial culture. The culture conditions of the transformant and the purification procedures of the enzyme are described below.

Culture of *Escherichia coli* Transformant

The bacterial strain was preliminarily cultured in a flask. The resulting liquid bacterial culture of 2 liters was inoculated in a 170-liter liquid culture medium sterilized in an autoclave, which was subjected to aeration agitation culture at 37° C. for 16 hours. At OD 600=1, 4 to 6 hours after the initiation of the culture, IPTG (isopropyl β-thiogalactoside) was added thereto at a final concentration of 0.5 mM, to induce the expression of the recombinant enzyme. At the end of the culture, the bacteria were separated and recovered by centrifugation, at a wet weight yield of 700 g, which contained about 500 kU of the enzyme.

| Culture medium composition: | LB culture medium, pH 7.5 |
| --- | --- |
| Yeast extract | 5 g/L |
| Tryptone | 10 g/L |
| NaCl | 5 g/L |
| Sodium ampicillin | 50 mg/L |

Purification of Recombinant Enzyme

By disrupting the cultured bacteria, the enzyme was extracted from the bacteria, which was then subjected to a combination of various chromatographic modalities, to recover a sample of the enzyme as identified as a single spot by electrophoresis. The purification procedures of the thermo-resistant isocitrate dehydrogenase are summarized as described below. Finally, an enzyme sample with a specific activity of 83.8 U/mg could be prepared.

| Purification Procedures | Protein (g) | Total Activity (kU) | Specific activity (U/mg) | Purification ratio |
| --- | --- | --- | --- | --- |
| Extraction & Thermal treatment at 60° C. | 141 | 508 | 3.6 | 1.0 |
| DEAE-Sepharose | 8.5 | 393 | 46.1 | 12.8 |
| Phenyl-Sepharose | 3.8 | 258 | 68.2 | 18.9 |
| AcA44 gel filtration | 3.0 | 250 | 83.8 | 23.3 |

Assay of Enzyme Activity

One unit of the enzyme was defined as the quantity with an activity to generate 1 μmol NADPH per one minute under the aforementioned assay conditions.

Assay temperature: 37° C.
Assay wave length: 340 nm

Substrate reaction solution:
    0.1 M Triethanol amine hydrochloric acid buffer, pH 8.0 containing 5 mM $MgCl_2$,
    5 mM isocitric acid 1 mM $NADP^+$.

After purification, the properties of the following three species of thermo-resistant ICD were compared to each other. ICD species derived from yeast: ICD derived from commercially available yeast (manufactured by Oriental Yeast, Co.) ICD species derived from genus Sulfolobus: ICD extracted and purified fromabacterial culture of *Sulfolobus acidocaldarius* (IFO 15157) (JP-A-9-295) ICD species derived from genus Thermus: thermo-resistant recombinant ICD derived from *Thermus aquaticus* (Example 1).

The results are shown in the following table.

Comparison of properties of purified enzymes

| Properties | Yeast-derived ICD | Sulfolobus-derived ICD | Thermus-derived ICD |
|---|---|---|---|
| Optimum pH | 8.5 | 7.5 | 8.5 |
| Temperature thermally stable | 50° C. | 80° C. | 80° C. |
| Cross reactivity with $NAD^{+*}$ | — | 5% | 15% |
| Stability under storage** | completely inactivated after 2-week storage at 37° C. | never inactivated after 2-week storage at 37° C. | never inactivated after 2-week storage at 37° C. |

Note:
*expressed as relative degree to the reactivity with $NADP^+$ as designated 100%.
**stability under storage at alkaline pH.

EXAMPLE 2

Assay of Urea Nitrogen Using Intact Urine Sample

Ammonia elimination reagents with addition of various isocitrate dehydrogenase species at various concentrations were prepared. The performance of these ammonia elimination reagents for intact urine was tested, in relation to various levels of isocitrate dehydrogenase species and ammonia elimination periods. The results are shown in the following table.

The time required for eliminating endogenous ammonia in intact urine-was defined as a time required for the absorbance A340 to resume the initial value at the time of addition of these reagents, after the start of the ammonia elimination reaction.

| | Ammonia elimination time for intact urine sample | |
|---|---|---|
| ICDH concentrations | Sulfolobus-derived | Thermus-derived |
| 0.1 U/ml | 8 min | 5 min |
| 0.2 | 6 | 4 |
| 0.5 | 5 | 2 |
| 1 | 3 | 1.5 |
| 2 | 2 | 1 |
| 5 | 1 | 1 |

Preparation of Ammonia Elimination Reagents
    Buffer: 10 mM sodium hydrogen carbonate buffer, pH 9.2.
    Concentrations of substrate and coenzyme added:
        10 mM isocitric acid
        7 mM 2-Oxoglutaric acid
        0.35 mM NADPH
        0.2 mM $MgCl_2$
    Quantity of enzyme added:
        20 U/ml glutamate dehydrogenase (commercially available)

Isocitrate dehydrogenase was added at such various concentrations as described in the above table.

Conditions for Ammonia Elimination Reaction
    Ratio of sample: reagent=3: 320 ($\mu$l)
    Sample: human pool urine (commercially available; manufactured by BioRad, CO.)
    Reaction temperature: 37° C.
    Assay wave length: 340 nm.
    Analyzer: Automatic analyzer, Hitachi 7150.

Figure 2:
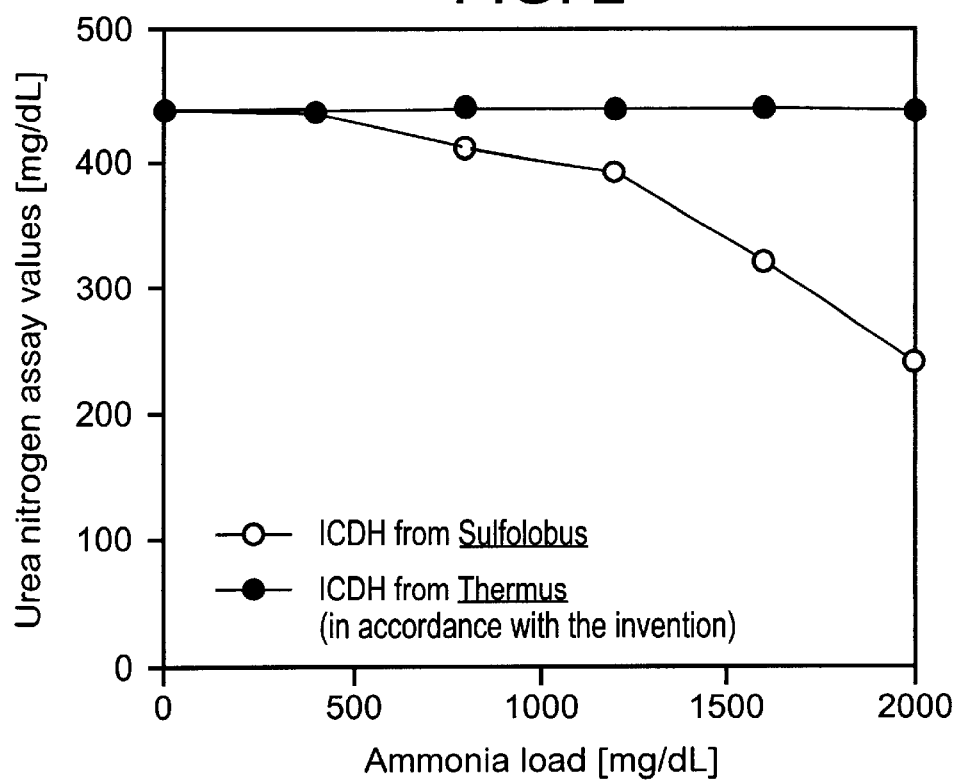
FIG. 2 shows the results of an assay under a load of endogenous ammonia at various quantities.

Using the ammonia elimination reagent as a first reagent solution and a urease reagent solution as a second reagent, urea nitrogen was assayed in an intact urine sample under the load of various levels of endogenous ammonia. 3 U/ml Isocitrate dehydrogenase was contained in the first reagent. The results are shown in FIG. 2.

EXAMPLE 3

The response to $NAD^+$ was tested with ammonia elimination reagents pre pared by using NADH, as described hereinbelow.

Assay of Cross Reactivity with $NAD^+$
    Reaction solution buffer:
        10 mM sodium hydrogen carbonate buffer, 9.2
    Concentrations of substrate and coenzyme added:
        10 mM isocitric acid
        7 mM 2-Oxoglutaric acid
        0.1 mM $NAD^+$ or $NADP^+$
        0.2 MM $MgCl_2$
    Quantity of enzyme added:
        various concentrations of isocitrate dehydrogenase (of the invention) and $NAD^+$-type isocitrate dehydrogenase derived from yeast as a control (manufactured by Oriental Yeast, Co.).
    Assay conditions: Adding various concentrations of isocitrate dehydrogenase to a reaction solution containing the coenzyme and substrates, and mixing the resulting mixture together, the reaction was initiated. The quantity of NAD(P)H in conversion 5 minutes after the initiation of the reaction at 37° C. was assayed as $\Delta A340$.

Figure 3:
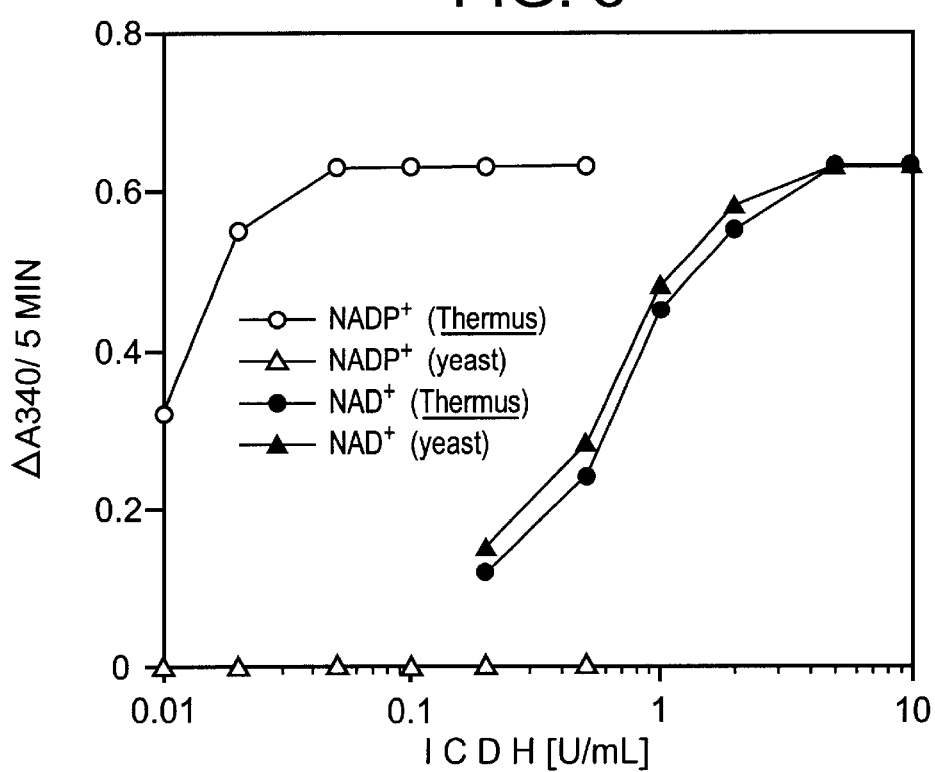
FIG. 3 depicts the relation between the quantity of the fed enzyme and the quantity of NAD(P)H in conversion.

Under such various conditions, the relation between the quantity of the enzyme added and the quantity of NAD(P)H in conversion was assayed and plotted in FIG. 3. It is apparently indicated that the inventive isocitrate dehydrogenase derived from *Thermus aquaticus* substantially has a cross reactivity with $NAD^+$ even at the alkaline pH.

Preparation of Ammonia Elimination Reagents
    Buffer: 10 mM sodium hydrogen carbonate buffer, pH 9.2
    Concentrations of substrate and coenzyme added:
        10 mM isocitric acid
        7 mM 2-Oxoglutaric acid
        0.35 mM NADH
        0.2 mM $MgCl_2$
    Quantity of enzyme added:
        20 U/ml glutamate dehydrogenase (NADH type, commercially available)
        5 U/ml isocitrate dehydrogenase (of the invention)

'Conditions for Ammonia Elimination Reaction
  Ratio of sample: reagent=3: 320 (μl)
  Sample: human pool urine (commercially available; manufactured by BioRad, CO.) loaded with various levels of endogenous ammonia.
  For elimination assay, a urine sample was preliminarily diluted 10-fold with physiological saline, which was used as a sample.
  Reaction temperature: 37° C.
  Assay wave length: 340 nm.
  Analyzer: Automatic analyzer, Hitachi 7150.

Using the ammonia elimination reagent as a first reagent solution and a urease reagent solution as a second reagent, the blocking degree of the influence of the endogenous ammonia at various levels was examined, on the basis of the urea nitrogen value assayed in the urine sample. The results are shown in the following table. The prepared ammonia elimination reagent in solution was tested under storage at 37° C. for one week, to compare the ammonia elimination performance with the ammonia elimination performance of the control after the storage test. The following table indicates that the *Thermus aguaticus*-derived isocitrate dehydrogenase exhibited great test results even after the isocitrate dehydrogenase was incorporated in the ammonia elimination reagent with NADH.

| Ammonia load (mg/dL) to human pool urine | Urea nitrogen assay | | | |
| --- | --- | --- | --- | --- |
| | urea nitrogen (mg/dL) on day 0 | % | urea nitrogen (mg/dL) after 37° C. × 1 week | % |
| 0 | 445 | 100.0 | 445 | 100.0 |
| 500 | 446 | 100.2 | 446 | 100.2 |
| 1000 | 445 | 100.0 | 448 | 100.7 |
| 1500 | 442 | 99.3 | 441 | 99.1 |
| 2000 | 430 | 96.7 | 425 | 95.5 |

By nucleotide substitution, a recombinant isocitrate dehydrogenase was prepared as follows; and then, the recombinant enzyme was prepared at a mass scale as described below.

EXAMPLE 4

Construction of plasmid for allowing *Thermus apuaticus*-derived isocitrate dehydrogenase to be expressed in *E. coli* For efficient expression in *E. coli*, gene sequences of *Thermus aquaticus*-derived isocitrate dehydrogenase were designed (SQ ID Nos. 1 and 3). For integration thereof in an expression vector, an EcoRI recognition sequence and a BamHI recognition sequence were introduced at the N terminus and C terminus, respectively. Additionally, some nucleotides were modified with optimum codons for *Escherichia coli*.

The nucleotide sequence of the gene of the *Thermus aquaticus*-derived isocitrate dehydrogenase and the amino acid sequence thereof are shown in SQ ID Nos. 3 and 1, respectively. The SQ ID No. 1 is the same as the amino acid sequence of the thermo-resistant ICD disclosed by the inventors in the prior application (JP8-328400); The SQ ID NO. 3 corresponds to the nucleotide sequence (SQ ID No. 2) of the thermo-resistant ICD gene disclosed by the inventors in the same prior application, except for the following substitutions: the second codon GCC and ninth codon CCC in the structural gene starting from the translation initiation codon ATG were substituted with GCT and CCG, respectively.

Figure 4:
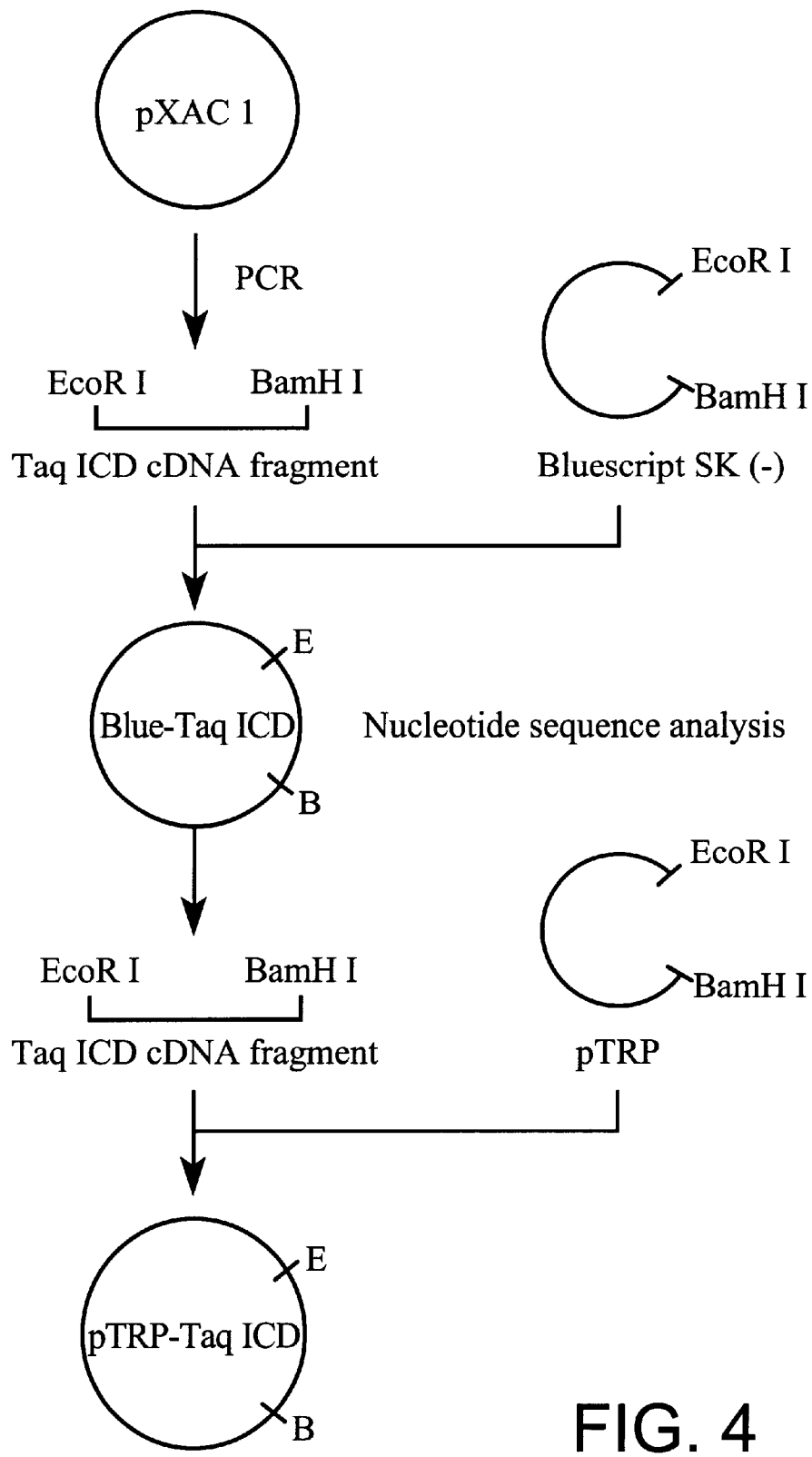
FIG. 4 depicts a construction chart of a high expression plasmid pTRP-Taq ICD.

Then, plasmid pTRP-Taq ICD with a thermo-resistant ICD DNA fragment inserted therein was prepared, following the construction chart shown in FIG. 4.

First, *Escherichia coli* was transformed with an expression plasmid pEXAC1 capable of expressing the thermo-resistant ICD; and from the resulting transformant (FERM BP-6704) plasmid pEXAC1 was separated. The plasmid carries a DNA fragment harboring the gene encoding the thermo-resistant ICD, which gene is derived from the chromosomal DNA of the *Thermus aquaticus* strain YT1 (ATCC 25104). The plasmid has successfully been developed by the inventors as described in the prior application.

Using the following two types of primers (sense primer and antisense primer), PCR was conducted, additionally using the DNA in the plasmid pEXAC1 as the template under the following conditions, for amplification of the cDNA, to recover a DNA fragment of the gene encoding the thermo-resistant ICD.

PCR conditions
  95° C. for 5 min, 55° C. for 30 sec and 72° C. for 1 min 30 sec
  →
  95° C. for 30 sec, 55° C. for 30 sec and 72° C. for 1 min 30 sec
  30 cycles
  →
  72° C. for 5 min and 4° C. forever.
Primer
Sense Primer
  5'-CCG GAATTCATGGCTTACCAGCGCATCCAGATTCC-GCAGGAGGGCGAAAAGATC-3'
  EcoRI
Antisense Primer
  5'-CCCGGATCC CTA TTAGTCCATGTGCTGGATCAGGGC-3'
  BamHI The underlined parts represent the restriction enzyme sites and the *Escherichia coli* optimum codon-modified sites.

Inserting the DNA fragment of the gene into EcoRI-/BamHI-digested pBluescript II SK (−) phagemid vector (STRATAGENE) followed by annealing, a recombinant plasmid Blue-Taq ICD was recovered and used for the transformation of *E. coli*. It was confirmed after the separation of the recombinant plasmid and the analysis of the nucleotide sequence that the sequence was the intended one.

Figure 5:
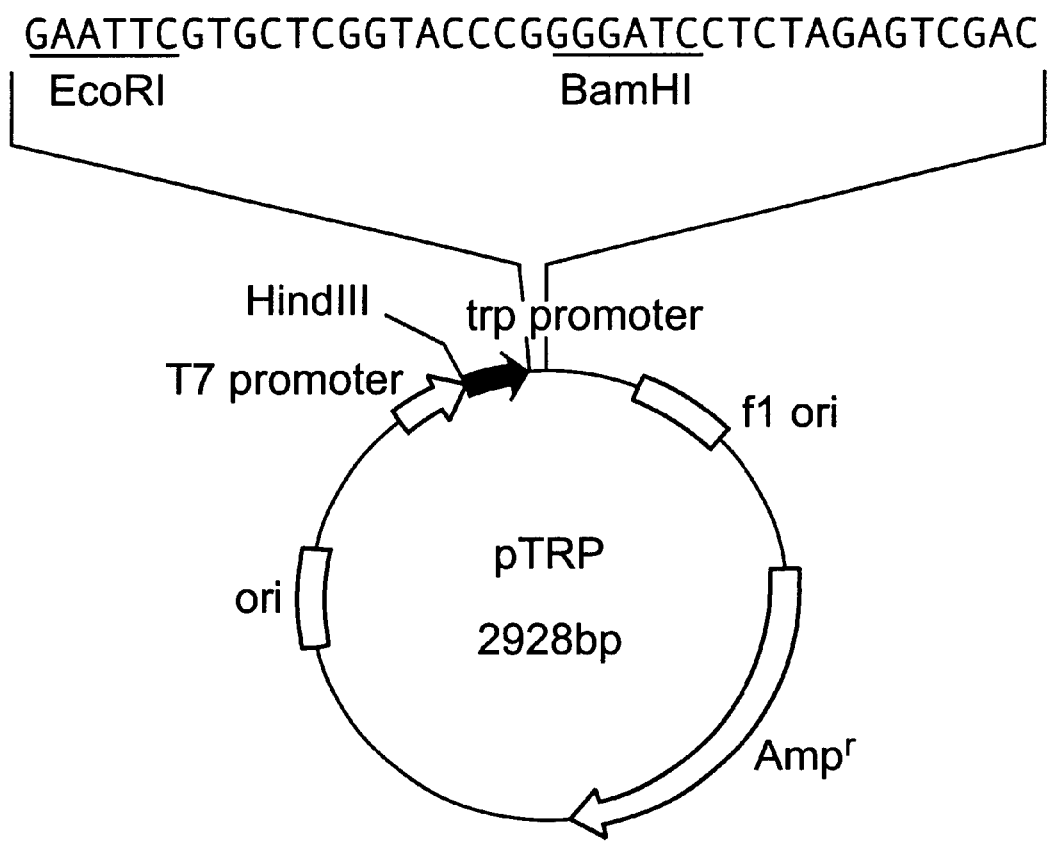
FIG. 5 depicts the structure of pTRP vector.

Inserting the EcoRI-/BamHI-digested fragment into an expression vector pTRP with a tryptophan promoter, followed by annealing, a recombinant plasmid pTRP-Taq ICD with the thermo-resistant ICD gene inserted therein was recovered. As the vector pTRP, expression vectors previously developed by the inventors (JP-A-8-103278 and JP-A-8-103279; the structure is shown in FIG. 5; transformants *Echerichia coli* JM101/pTRAL-112 and *Echerichia coli* JM109/pTRP/hMb have been deposited as FERM BP-4818 and FERM BP-5181, on Oct. 5, 1994 and Jul. 28, 1995, respectively, in National Institute of Bioscience and Human-Technology, Agency of Industrial Science and Technology) were used in the example after the expression vectors were preliminarily digested with EcoRI and BamHI.

By replacing the termination codon TGA of the structural gene in the nucleotide sequence of SQ ID No. 2 with the termination codon TAA with the highest termination efficiency of translation in *Echerichia coli* and conjugating an additional termination codon TAG to the nucleotide sequence, a gene sequence was designed, which is shown as the nucleotide sequence of SQ ID No. 4.

By using the thus recovered recombinant plasmid pTRP-Taq ICD, an *Echerichia coli* strain JM109 was transformed. The plasmid in the resulting transformant was separated by the alkali-SDS method. It was confirmed by restriction cleavage that the objective gene was inserted in the plasmid. Again, the *E. coli* strain JM109 was transformed. A transformant was recovered.

In such manner, the *E. coli* strain JM109 transformed with the plasmid pTRP-Taq ICD was designated *Escherichia coli* JM109/pTRP-Taq ICD and deposited as FERM BP-6365 in National Institute of Bioscience and Human-Technology, Agency of Industrial Science and Technology.

EXAMPLE 5

Mass-scale production of thermo-resistant isocitrate dehydrogenase derived from *Thermus acuaticus* by high-density transformant culturing (high-density culturing by fed batch culture)

A transformant FERM BP-6365 of *Echerichia coli* strain JM109, which was prepared by transformation with the plasmid pTRP-Taq ICD, was subjected to high-density culture by using 16L New Brunswick Scientific Fermenter SF-116 (Edison, N.J., USA) Culture parameters including temperature, pH, agitation velocity and aeration volume were controlled to 37° C., pH 7.4, 800 rpm and 15 ml/min by means of ML-4100 (Multi-loop microprocessor controller) . With addition of an aqueous 10% ammonia, pH was adjusted.

After overnight pre-culturing, the culture of 240 ml was inoculated in an LB culture medium of 8 liters containing 25 μg/ml ampicillin, for 2-hr culturing. Thereafter, a feed culture medium was continuously fed to the culture under culturing for up to 10 hours, to a final volume of 2 liters.

The feed culture medium had the following composition. Feed Culture Medium, pH 7.4
  10% glucose
  15% yeast extract
  0.1% $MgSO_4 \cdot 7H_2O$
  0.75% L-glutamic acid
  0.75% L-threonine
  0.04% L-tyrosine
  0.4% L-histidine
  0.4% L-methionine.

The culture medium was fed to the culture, initially at a velocity of 100 ml/h; every 2 hours, then, the velocity was changed and increased to 200 ml/h, 300 ml/h and 400 ml/h, sequentially. Twelve hours later, the bacteria were collected by centrifugation (11,000 g×20 min). The bacterial proliferation was examined by measuring the absorbance of the culture at 600 nm After the high-density culturing, consequently, the transformant (FERM BP-6365) of the *Echerichia coli* strain JM109 was recovered, which transformant had been prepared by transformation with the plasmid pTRP-Taq ICD.

Expression level of isocitrate dehydrogenase per unit bacterial quantity by high-density culturing in comparison with control level The following production yields are compared to each other as shown below in the table; the production yield of isocitrate dehydrogenase per unit bacterial quantity of the inventive transformant by high-density culturing (the inventive method), the production yield thereof per unit bacterial quantity of the transformant described in JP8-328400 as cultured by high-density culturing (control 1) and the production yield thereof per unit bacterial quantity of the inventive transformant as cultured by batch culturing in the essential LB culture medium (control 2) (the latter two bacterial cultures were controls).

TABLE

| Bacteria | OD600 | Production yield per culture (liter) | Specific activity of extract solution |
| --- | --- | --- | --- |
| Control 1 | 3 | 1200 U/L | 5.05 U/mg · protein |
| Control 2 | 9 | 2000 U/L | 4.57 U/mg · protein |
| Invention | 35 | 20000 U/L | 8.68 U/mg · protein |

For calculating the ICD production yield per unit volume of cultured bacteria, a culture suspension (2 ml) was sampled at the end of culturing, which was centrifuged; to the resulting bacterial pellet was added an extraction buffer of 1 ml of 10 mM potassium phosphate ($K-PO_4$) buffer, pH 7.5 containing 1 mM mercaptoethanol, 0.5 mM EDTA, 0.02% $NaN_3$ and 0.1 mM PMSF, so as to suspend again the pellet in the buffer; then, the resulting suspension was subjected to ultrasonic disruption under cooling in ice. After re-centrifugation, the activity of isocitrate dehydrogenase extracted and solubilized in the resulting supernatant was assayed under the following conditions.

Assay of activity of isocitrate dehydrogenase
Assay wave length: 340 nm
Assay temperature: 37° C.
Substrate reaction solution:
  100 mM TEA-HCl buffer, pH 8.0
  5 MM $MgCl_2$
  5 mM Potassium isocitrate
  0.5 MM $NADP^+$.

One unit of isocitrate dehydrogenase was defined as the quantity generating 1 pmole NADPH per minute.

Figure 6:
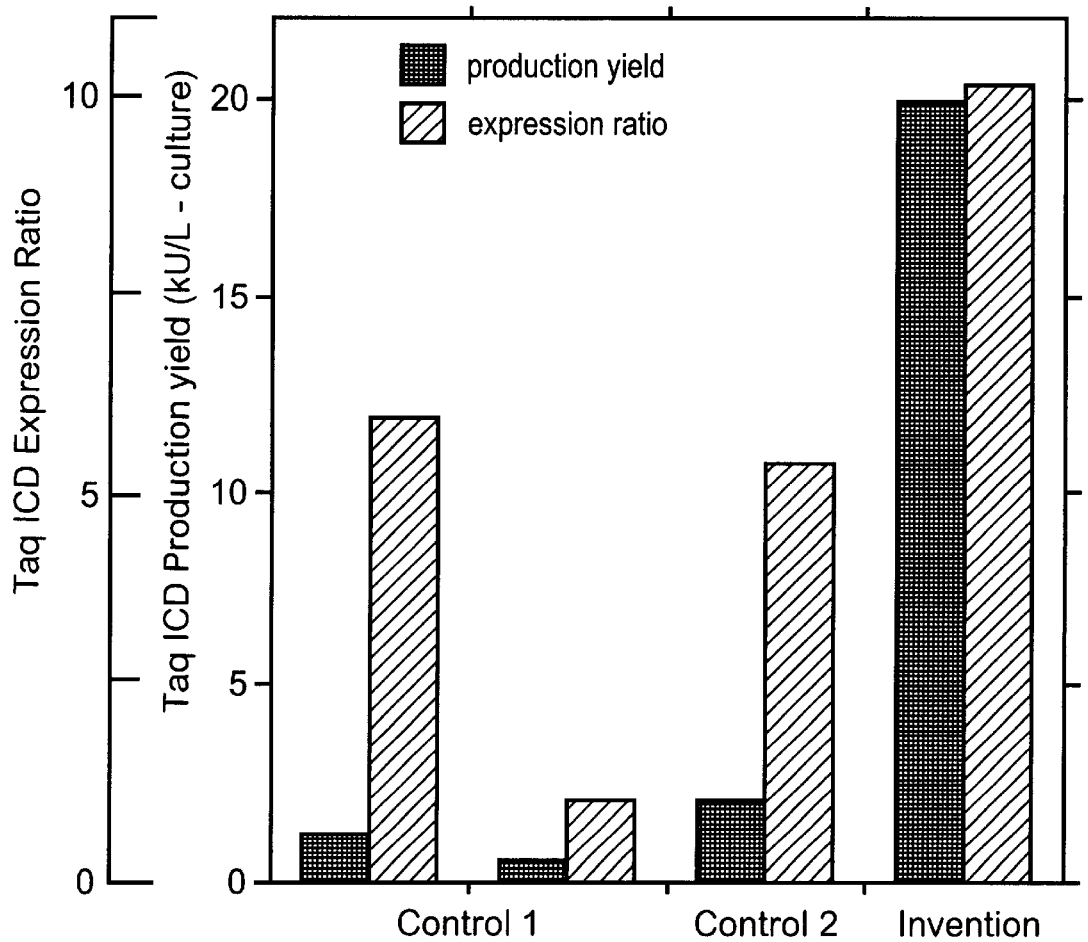
FIG. 6 depicts the relation between the quantity of generated isocitrate dehydrogenase and the expression ratio of the recombinant enzyme per unit volume of cultured bacteria under various culture conditions (control 1, control 2 and inventive method).

As apparently shown in the above table and FIG. 6, the production yield of isocitrate dehydrogenase per unit bacterial quantity can be elevated 10-fold or more by the inventive high-density culture method (these apparently indicate that the inventive transformant cultured by high-density culturing attained far greater results, compared with the control 1 cultured by the same high-density culturing); the specific activity per protein extracted and solubilized from bacteria cultured by the high-density culturing was increased by about 2 fold, suggesting that the resulting cultured bacteria were effectively purified. FIG. 6 shows the relation between the production yield of isocitrate dehydrogenase under various culture conditions (controls 1 and 2 and invention) and the expression ratio of the recombinant enzyme per cultured bacterium. In the figure, the expression ratio per cultured bacterium is calculated and expressed as specific activity of extract solution/specific activity of purified enzyme (100 U/mg).

EFFECTS OF THE INVENTION

According to the invention, an ammonium elimination liquid reagent can readily be prepared by using such thermo-resistant isocitrate dehydrogenase with prominent stability under alkaline conditions suitable for the ammonium elimination liquid reagent. Thus, such novel ammonium elimination liquid reagent is stable under long-term storage.

Because the thermo-resistant isocitrate dehydrogenase with such an excellent characteristic property as responsiveness to both $NADP^+$ and $NAD^+$ is used in accordance with the invention, NADH never possibly used in the conventional ammonia elimination liquid reagents in spite of the economical advantage can thus be incorporated into the assay system; the thermo-resistant isocitrate dehydrogenase can be used in combination with NADH and additionally in combination with NADPH conventionally used, effectively for the designing of analytical reagents, so kits can readily be designed for the assay system. Furthermore, ammonia can be eliminated for an extremely short time, by using the enzyme. Therefore, persons engaged in laboratory tests highly acclaim the inventive ammonia elimination reagent. Thus, the ammonia elimination reagent is practical.

In accordance with the invention, preferably, use is made of for example thermo-resistant isocitrate dehydrogenase derived from the genus Thermus as the thermo-resistant isocitrate dehydrogenase; additionally, a recombinant thermo-resistant isocitrate dehydrogenase can be produced at a mass scale.

SEQUENCE LISTING

The amino acid sequence (SQ ID No. 1) of a thermo-resistant ICD is shown in Tables 1, 2 and 3; the nucleotide sequence (SQ ID No. 2) of the DNA of the gene encoding the thermo-resistant ICD is shown in Tables 4, 5, 6, 7, 8 and 9; the nucleotide sequence (SQ ID No. 3) of the DNA of the structural gene encoding a recombinant thermo-resistant ICD of the invention is shown in Tables 10, 11, 12, and 13; and the nucleotide sequence (SQ ID No. 4) of the DNA of the structural gene encoding a recombinant thermo-resistant ICD of the invention is shown in Tables 14, 15, 16, and 17.

TABLE 1

Sequence listing
Sequence ID No.1
Sequence length: 426
Sequence type: amino acid
Molecular type: double-strandedness
Topology: linear
Sequence species: peptide
Sequence Met Ala Tyr Gln Arg Ile Gln Ile Pro Gln Glu Gly Glu Lys Ile Thr
 1           5                   10                  15

Ile Gln Glu Gly Val Leu Lys Val Pro Asp Gln Pro Ile Ile Gly Phe
            20                  25                  30

Ile Glu Gly Asp Gly Thr Gly Pro Asp Ile Trp Arg Ala Ala Gln Pro
            35                  40                  45

Val Leu Asp Ala Ala Val Ala Lys Ala Tyr Gly Gly.Gln Arg Arg Ile
        50                  55                  60

Val Trp Val Glu Leu Tyr Ala Gly Glu Lys Ala Asn Gln Val Tyr Gly
 65                 70                  75                  80

Glu Pro Ile Trp Leu Pro Glu Glu Thr Leu Glu Phe Ile Arg Glu Tyr
                85                  90                  95

Leu Val Ala Ile Lys Gly Pro Leu Thr Thr Pro Val Gly Gly Gly Ile
               100                 105                 110

TABLE 2

Arg Ser Ile Asn Val Ala Leu Arg Gln Glu Leu Asp Leu Tyr Ala Cys
        115                 120                 125

Val Arg Pro Val Arg Trp Phe Gln Gly Val Pro Ser Pro Val Lys His
        130                 135                 140

Pro Glu Leu Val Asn Met Val Ile Phe Arg Glu Asn Thr Glu Asp Ile
145                 150                 155                 160

Tyr Ala Gly Ile Glu Trp Pro Ala Gly Ser Glu Val Lys Lys Val
                165                 170                 175

Leu Asp Phe Leu Lys Arg Glu Phe Pro Lys Ala Tyr Ala Lys Ile Arg
            180                 185                 190

Phe Pro Glu Thr Ser Gly Leu Gly Leu Lys Pro Ile Ser Lys Glu Gly
        195                 200                 205

Thr Glu Arg Leu Val Glu Ala Ala Ile Glu Tyr Ala Ile Lys Glu Asp
        210                 215                 220

Leu Pro Ser Val Thr Leu Val His Lys Gly Asn Ile Met Lys Phe Thr
225                 230                 235                 240

Glu Gly Ala Phe Arg Glu Trp Gly Tyr Ala Leu Ala Arg Glu Lys Tyr
            245                 250                 255

TABLE 2-continued

```
Gly Ala Thr Pro Leu Asp Gly Gly Pro Trp His Val Leu Lys Asn Pro
        260                 265                 270

Arg Thr Gly Arg Glu Ile Val Ile Lys Asp Met Ile Ala Asp Asn Phe
        275                 280                 285

Leu Gln Gln Ile Leu Leu Arg Pro Asp Glu Tyr Ser Val Ile Ala Thr
        290                 295                 300
```

TABLE 3

```
Met Asn Leu Asn Gly Asp Tyr Ile Ser Asp Ala Leu Ala Ala Gln Val
305                 310                 315                 320

Gly Gly Ile Gly Ile Ala Pro Gly Ala Asn Ile Asn Tyr Lys Thr Gly
        325                 330                 335

His Ala Val Phe Glu Ala Thr His Gly Thr Ala Pro Lys Tyr Ala Gly
        340                 345                 350

Gln Asp Lys Val Asn Pro Ser Ser Val Ile Leu Ser Gly Glu Met Met
        355                 360                 365

Leu Arg Tyr Leu Gly Trp Asn Glu Ala Ala Asp Leu Ile Ile Arg Ala
        370                 375                 380

Met Glu Arg Thr Ile Ser Lys Gly Leu Val Thr Tyr Asp Phe His Alg
385                 390                 395                 400

Leu Leu Val Ala Glu Gly Lys Pro Ala Thr Leu Leu Lys Thr Ser Glu
                405                 410                 415

Phe Gly Gln Ala Leu Ile Gln His Met Asp ***
        420                 425
```

TABLE 4

Sequence ID No. 2
Sequence length: 2872
Sequence type: nucleic acid
Molecular type: double-strandedness
Topology: linear

TABLE 4-continued

Sequence species: genomic DNA
Origin:
Name of organism: *Thermus aquaticus*
Name of strain: YT1 (ATCC 25104)
Sequence

TABLE 5

```
GCTCCTTCCC GTGGACCCCT GGGCGAAGGT GGCCTCCTTC TCCAAAAGGA GGACCTTAAG    60

CCCCGCCTCC GCTAGCCGGT AGGCCGAGGC CGCCCCTACG ATCCCCGCCC CCACCACCAG   120

CACATCCGCC ACCTCCCCAG TTTAGGAAGC CGGGAGTATG CTAGGCCCCG GAGGTACCT   179

ATG GCG TAC CAG CGC ATC CAG ATT CCC CAG GAG GGC GAA AAG ATC ACC    227
Met Ala Tyr Gln Arg Ile Gln Ile Pro Gln Glu Gly Glu Lys Ile Thr
 1                   5                  10                  15

ATC CAA GAG GGC GTC CTG AAG GTG CCG GAC CAG CCC ATC ATC GGC TTC    275
Ile Gln Glu Gly Val Leu Lys Val Pro Asp Gln Pro Ile Ile Gly Phe
                20                  25                  30

ATT GAG GGG GAT GGG ACC GGC CCT GAC ATC TGG AGA GCG GCC CAA CCC    323
Ile Glu Gly Asp Gly Thr Gly Pro Asp Ile Trp Arg Ala Ala Gln Pro
            35                  40                  45

GTC CTA GAC GCC GCC GTG GCC AAA GCC TAC GGC GGG CAA CGG CGC ATC    371
Val Leu Asp Ala Ala Val Ala Lys Ala Tyr Gly Gly Gln Arg Arg Ile
        50                  55                  60
```

TABLE 5-continued

| | | | | | | | | | | | | | | | |
|---|---|---|---|---|---|---|---|---|---|---|---|---|---|---|---|
| GTC | TGG | GTG | GAG | CTT | TAC | GCC | GGG | GAA | AAG | GCC | AAC | CAG | GTC | TAC | GGG | 419 |
| Val | Trp | Val | Glu | Leu | Tyr | Ala | Gly | Glu | Lys | Ala | Asn | Gln | Val | Tyr | Gly |
| 65 | | | | 70 | | | | | 75 | | | | | 80 | |

| | | | | | | | | | | | | | | | |
|---|---|---|---|---|---|---|---|---|---|---|---|---|---|---|---|
| GAG | CCC | ATC | TGG | CTC | CCC | GAG | GAG | ACC | CTG | GAG | TTC | ATC | CGG | GAG | TAC | 467 |
| Glu | Pro | Ile | Trp | Leu | Pro | Glu | Glu | Thr | Leu | Glu | Phe | Ile | Arg | Glu | Tyr |
| | | | | 85 | | | | | 90 | | | | | 95 | |

| | | | | | | | | | | | | | | | |
|---|---|---|---|---|---|---|---|---|---|---|---|---|---|---|---|
| CTG | GTG | GCC | ATC | AAG | GGC | CCC | CTG | ACC | ACG | CCG | GTG | GGC | GGC | GGC | ATC | 515 |
| Leu | Val | Ala | Ile | Lys | Gly | Pro | Leu | Thr | Thr | Pro | Val | Gly | Gly | Gly | Ile |
| | | | | 100 | | | | | 105 | | | | | 110 | |

TABLE 6

| | | | | | | | | | | | | | | | |
|---|---|---|---|---|---|---|---|---|---|---|---|---|---|---|---|
| CGG | AGC | ATC | AAC | GTG | GCC | CTC | AGG | CAG | GAG | CTG | GAC | CTC | TAC | GCC | TGC | 563 |
| Arg | Ser | Ile | Asn | Val | Ala | Leu | Arg | Gln | Glu | Leu | Asp | Leu | Tyr | Ala | Cys |
| | | | 115 | | | | | 120 | | | | | 125 | | |

| | | | | | | | | | | | | | | | |
|---|---|---|---|---|---|---|---|---|---|---|---|---|---|---|---|
| GTG | CGC | CCC | GTG | CGC | TGG | TTC | CAG | GGG | GTG | CCC | AGT | CCG | GTG | AAG | CAC | 611 |
| Val | Arg | Pro | Val | Arg | Trp | Phe | Gln | Gly | Val | Pro | Ser | Pro | Val | Lys | His |
| | 130 | | | | | 135 | | | | | 140 | | | | |

| | | | | | | | | | | | | | | | |
|---|---|---|---|---|---|---|---|---|---|---|---|---|---|---|---|
| CCG | GAG | CTG | GTC | AAC | ATG | GTC | ATC | TTC | CGG | GAG | AAC | ACC | GAG | GAC | ATC | 659 |
| Pro | Glu | Leu | Val | Asn | Met | Vai | Ile | Phe | Arg | Glu | Asn | Thr | Glu | Asp | Ile |
| 145 | | | | | 150 | | | | | 155 | | | | | 160 |

| | | | | | | | | | | | | | | | |
|---|---|---|---|---|---|---|---|---|---|---|---|---|---|---|---|
| TAC | GCC | GGG | ATT | GAG | TGG | CCG | GCG | GGG | AGC | GAG | GAG | GTA | AAG | AAG | GTC | 707 |
| Tyr | Ala | Gly | Ile | Glu | Trp | Pro | AIa | Gly | Ser | Glu | Glu | Val | Lys | Lys | Val |
| | | | | 165 | | | | | 170 | | | | | 175 | |

| | | | | | | | | | | | | | | | |
|---|---|---|---|---|---|---|---|---|---|---|---|---|---|---|---|
| CTA | GAC | TTC | TTG | AAG | CGG | GAG | TTC | CCC | AAG | GCC | TAC | GCC | AAG | ATC | CGC | 755 |
| Leu | Asp | Phe | Leu | Lys | Arg | Glu | Phe | Pro | Lys | Ala | Tyr | Ala | Lys | Ile | Arg |
| | | | 180 | | | | | 185 | | | | | 190 | | |

| | | | | | | | | | | | | | | | |
|---|---|---|---|---|---|---|---|---|---|---|---|---|---|---|---|
| TTC | CCC | GAG | ACC | TCG | GGC | CTG | GGC | CTG | AAG | CCC | ATC | TCC | AAG | GAG | GGC | 803 |
| Phe | Pro | Glu | Thr | Ser | Gly | Leu | Gly | Leu | Lys | Pro | Ile | Ser | Lys | Glu | Gly |
| | | 195 | | | | | 200 | | | | | 205 | | | |

| | | | | | | | | | | | | | | | |
|---|---|---|---|---|---|---|---|---|---|---|---|---|---|---|---|
| ACG | GAG | CGC | CTG | GTG | GAG | GCG | GCC | ATT | GAG | TAC | GCC | ATC | AAG | GAG | GAC | 851 |
| Thr | GLu | Arg | Leu | Val | Glu | Ala | Ala | Ile | Glu | Tyr | Ala | Ile | Lys | Glu | Asp |
| | 210 | | | | | 215 | | | | | 220 | | | | |

| | | | | | | | | | | | | | | | |
|---|---|---|---|---|---|---|---|---|---|---|---|---|---|---|---|
| CTC | CCC | AGC | GTG | ACC | CTG | GTC | CAC | AAA | GGC | AAC | ATC | ATG | AAG | TTC | ACC | 899 |
| Leu | Pro | Ser | Val | Thr | Leu | Val | His | Lys | Gly | Asn | Ile | Met | Lys | Phe | Thr |
| 225 | | | | | 230 | | | | | 235 | | | | | 240 |

TABLE 7

| | | | | | | | | | | | | | | | |
|---|---|---|---|---|---|---|---|---|---|---|---|---|---|---|---|
| GAA | GGG | GCC | TTC | CGG | GAG | TGG | GGC | TAC | GCC | CTG | GCC | CGG | GAA | AAG | TAC | 947 |
| Glu | Gly | Ala | Phe | Arg | Glu | Trp | Gly | Tyr | Ala | Leu | Ala | Arg | Glu | Lys | Tyr |
| | | | | 245 | | | | | 250 | | | | | 255 | |

| | | | | | | | | | | | | | | | |
|---|---|---|---|---|---|---|---|---|---|---|---|---|---|---|---|
| GGG | GCC | ACG | CCC | CTG | GAC | GGC | GGG | CCC | TGG | CAC | GTC | CTC | AAA | AAC | CCC | 995 |
| Gly | Ala | Thr | Pro | Leu | Asp | Gly | Gly | Pro | Trp | His | Val | Leu | Lys | Asn | Pro |
| | | | 260 | | | | | 265 | | | | | 270 | | |

| | | | | | | | | | | | | | | | |
|---|---|---|---|---|---|---|---|---|---|---|---|---|---|---|---|
| CGC | ACC | GGC | AGG | GAG | ATC | GTT | ATC | AAG | GAC | ATG | ATC | GCC | GAC | AAC | TTC | 1043 |
| Arg | Thr | Gly | Arg | Glu | Ile | Val | Ile | Lys | Asp | Met | Ile | Ala | Asp | Asn | Phe |
| | | 275 | | | | | 280 | | | | | 285 | | | |

| | | | | | | | | | | | | | | | |
|---|---|---|---|---|---|---|---|---|---|---|---|---|---|---|---|
| CTG | CAG | CAG | ATC | CTC | CTC | CGC | CCC | GAC | GAA | TAC | TCG | GTG | ATC | GCC | ACC | 1091 |
| Leu | Gln | Gln | Ile | Leu | Leu | Arg | Pro | Asp | Glu | Tyr | Ser | Val | Ile | Ala | Thr |
| | 290 | | | | | 295 | | | | | 300 | | | | |

| | | | | | | | | | | | | | | | |
|---|---|---|---|---|---|---|---|---|---|---|---|---|---|---|---|
| ATG | AAC | CTG | AAC | GGG | GAC | TAC | ATC | TCC | GAT | GCC | CTG | GCC | GCC | CAG | GTG | 1139 |
| Met | Asn | Leu | Asn | Gly | Asp | Tyr | Ile | Ser | Asp | Ala | Leu | Ala | Ala | Gln | Val |
| 305 | | | | | 310 | | | | | 315 | | | | | 320 |

| | | | | | | | | | | | | | | | |
|---|---|---|---|---|---|---|---|---|---|---|---|---|---|---|---|
| GGG | GGC | ATC | GGC | ATC | GCC | CCC | GGG | GCC | AAC | ATC | AAC | TAC | AAG | ACG | GGC | 1187 |
| Gly | Gly | Ile | Gly | Ile | Ala | Pro | Gly | Ala | Asn | Ile | Asn | Tyr | Lys | Thr | Gly |
| | | | | 325 | | | | | 330 | | | | | 335 | |

TABLE 7-continued

```
CAC GCC GTC TTT GAG GCC ACC CAC GGC ACC GCC CCC AAG TAC GCT GGC   1235
His Ala Val Phe Glu Ala Thr His Gly Thr Ala Pro Lys Tyr Ala Gly
            340                 345                 350

CAG GAC AAG GTG AAC CCC AGC AGC GTC ATC CTC TCC GGG GAG ATG ATG   1283
Gln Asp Lys Val Asn Pro Ser Ser Val Ile Leu Ser Gly Glu Met Met
            355                 360                 365
```

TABLE 8

```
CTT CGC TAC CTG GGC TGG AAC GAG GCG GCG GAC CTC ATC ATC AGG GCC   1331
Leu Arg Tyr Leu Gly Trp Asn Glu Ala Ala Asp Leu Ile Ile Arg Ala
            370                 375                 380

ATG GAG AGG ACC ATC AGC AAG GGC CTG GTC ACC TAC GAC TTC CAC CGC   1379
Met Glu Arg Thr Ile Ser Lys Gly Leu Val Thr Tyr Asp Phe His Arg
385                 390                 395                 400

CTC CTG GTG GCC GAG GGC AAG CCC GCC ACG CTT CTT AAG ACC AGC GAG   1427
Leu Leu Val Ala Glu Gly Lys Pro Ala Thr Leu Leu Lys Thr Ser Glu
                405                 410                 415

TTC GGC CAG GCC CTG ATC CAG CAC ATG GAC TGA AAACGTTTGG GGCCCCCGCC  1480
Phe Gly Gln Ala Leu Ile Gln His Met Asp ***
                420                 425

GTGGCAAAAG CCACGGCGGG GTGCTTAGAC CAGGGCGAAG CGGGCCTCGA GGGCCGGAAG  1540

GTCCGCCTCC AGGAAGCGGA GGCGGACCTC GGCGTTGAGG GCAAGAGGCC CGGAGAGGGC  1600

CACCTGGGCG AAAGCCCGA GCTCCGGGAG GAGGAAGACC CCCTGTCCCC CCGGCCTCTC   1660

CACCAGGACG CCCGGGCCCT CGTAGCCCTT TTCCATCAGG TAGAGGAGGG TCCAGTGGAG  1720

CTTGCTCCGC CTCTCCCCTT CCCGCACCAG GTCGGCCACC GCCTCCGCCG CCCCCACCCG  1780

CTCCAGGACC TCCCCCTGGG AAAGGGGCCT TTCCCCCTTG AGCCAGGCCC TGAGCTGCTG  1840

GTGAGCCACC AGGTCCAGGT AGCGCCTTAA GGGGCTCGTC ACCTGGGCGT AGAGGGGAAG  1900

GCCGAGGCCC CGGTGGGGGG CGGGGACGGCC TTGAGCTGCG CCCTCTTCA GGGTCTTCCG   1960

CTGCGCCCAC ATGGCGGCGA GGCCCTCCCCC TCCACCCGGT GGGAAGGGGC CTCCTGGGT   2020

GGCGAAGGGA AAGGGAAGGC CCTCCCTCAGG GCCAGGTGGG CGGCGCGTAG GCGAAGGAG   2080

CATGGCCTCC CGCACCCAGA CCCGGCTTTCA TAGGGGGGAA GGGGGGTGAT CCGGATCTC   2140

CTCCCCCTCC ACCCGAACCT TGACCTCGGGC AGGGCGATGT CCAAAGCCCC CTGGGCCAG   2200
```

TABLE 9

```
GCGCTTCCGA AAAAAGTCCC CCGCCAAGGCC TTCATGGGCG CCAGGGCCTC CACCTCGAG   2260

GGCTCCCGGT AGAAAGCCGC CTCACCCGCAC CCAGGAGAGG TAAAGGTCCT CCCGCAAAA   2320

GGCTCCTTCC GGGGAGACCA GAAGCTCAAAG GTGAGGGCTG GGGAGACCTC CTTAAGCCC   2380

CAGCCCAGGG CCTCGGTCAC CGCCAGGGGA GCATGGGCAC CGTGCCCTCG GCAGATAG    2440

AGGTTGGCCC CCCGGCGGAG GGCCTCCTGGT CCAGGGGGCT TCCCGGCCCG ACCAAAGC   2500

GCCACATCGG CCACATGGAC GAAAAGGTGGA AGCCCTCCTC CACCCTTTCG GCGTAAAGG  2560

GCGTCGTCCG GGTCCTGGCT CCCCTCGTCGT CAATGGCGAA GGCGGGGAGG TGGGTGAGG  2620

TCCACCCGCT CCTCCTCGGG CAGGGGGGGA CGGGGAGGTC CGGCGGGCC AGGGGAAGG    2680

CCAAGCCGCC TGGGGTGGGG GTTTTCCCGCC GCCAGAGGCC CAGGCGGAGA AGGAGCCGT  2740

GGGCGGCCTC GGGGGTTTCG GGAAGGCCCAG GGCCTTGAGA AGCCGGCTTT CCTTCCTCT  2800
```

TABLE 9-continued

CGCCGTGGGC CAGAGCCTCC ACCTCGGCCAG GAGGGGGCGG TCCTCGAGGG AGGGCCGTC  2860

CCTGGCGGAT CC  2872

TABLE 10

Sequence ID No. 3
Sequence length: 1281
Sequence type: nucleic acid
Molecular type: double-strandedness
Topology: linear
Sequence species: another nucleic acid, synthetic DNA
Origin:
Name of organism: *Thermus aquaticus*
Name of strain: YT1 (ATCC 25104)
Sequence characteristics
Symbol expressing the characteristics: structural gene
Method for identifying the characteristics: S
Sequence

```
ATG GCT TAC CAG CGC AJC CAG ATJ CCG CAG GAG GGC GAA AAG ATC ACC    48
Met Ala Tyr Gln Arg Jle Gln Ile Pro Gln Glu Gly Glu Lys Ile Thr
 1               5                  10                  15

ATC CAA GAG GGC GTC CTG AAG GTG CCG GAC CAG CCC ATC ATC GGC TTC    96
Ile Gln Glu Gly Val Leu LYs VaL Pro Asp Gln Pro Ile Ile Gly Phe
            20                  25                  30

ATT GAG GGG GAT GGG ACC GGC CCT GAC ATC TGG AGA GCG GCC CAA CCC   144
Ile Glu Gly Asp Gly Thr Gly Pro Asp Ile Trp Arg Ala Ala Gln Pro
        35                  40                  45
```

TABLE 11

```
GTC CTA GAC GCC GCC GTG GCC AAA GCC TAC GGC GGG CAA CGG CGC ATC   192
Val Leu Asp Ala Ala Val Ala Lys Ala Tyr Gly Gly Gln Arg Arg Ile
        50                  55                  60

GTC TGG GTG GAG CTW TAC GCC GGG GAA AAG GCC AAC CAG GTC TAC GGG   240
Val Trp Val Glu Leu Tyr Ala GlY Glu Lys Ala Asn Gln Val Tyr GJy
 65                  70                  75                  80

GAG CCC ATC TGG CTC CCC GAG GAG ACC CTG GAG TTC ATC CGG GAG TAC   288
Glu Pro IIe Trp Leu Pro Glu Glu Thr Leu Glu Phe Ile Arg Glu Tyr
                85                  90                  95

CTG GTG GCC ATC AAG GGC CCC CTG ACC ACG CCG GTG GGC GGC GGC ATC   336
Leu Val Ala Ile Lys Gly Pro Leu Thr Thr Pro Val Gly Gly Gly Ile
            100                 105                 110

CGG AGC ATC AAC GTG GCC CTC AGG CAG GAG CTG GAC CTC TAC GCC TGC   384
Arg Set Ile Asn Val Ala Leu Arg Gln Glu Leu Asp Leu Tyr Ala Cys
        115                 120                 125

GTG CGC CCC GTG CGC TGG TTC CAG GGG GTG CCC AGT CCG GTG AAG CAC   432
Val Arg Pro Val Arg Trp Phe Gln Gly Val Pro Ser Pro VaJ Lys His
    130                 135                 140

CCG GAG CTG GTC AAC ATG GTC ATC TTC CGG GAG AAC ACC CAG GAC ATC   480
Pro Glu Leu Val Asn Met Val Ile Phe Arg Glu Asn Thr GJu Asp Ile
145                 150                 155                 160

TAC GCC GGG ATT GAG TGG CCG GCG GGG AGC GAG GAG GTA AAG AAG GTC   528
Tyr Ala Gly Ile Glu Trp Pro Ala Gly Ser GJu GJu Val Lys Lys Val
                165                 170                 175
```

TABLE 12

```
CTA GAC TTC TTG AAG CGG GAG TTC CCC AAG GCC TAC GCC AAG ATC CGC    576
Leu Asp Phe Leu Lys Arg Glu Phe Pro Lys Ala Tyr Ala Lys Ile Arg
        180                 185                 190

TTC CCC GAG ACC TCG GGC CTG GGC CTG AAG CCC ATC TCC AAG GAG QGC    624
Phe Pro Glu Thr Ser Gly Leu Gly Leu Lys Pro Ile Ser Lys Glu Gly
        195                 200                 205

ACG GAG CGC CTG GTG GAG GCG GCC ATT GAG TAC GCC ATC AAG GAG GAC    672
Thr Glu Arg Leu Val Glu Ala Ala Ile Glu Tyr Ala Ile Lys Glu Asp
        210                 215                 220

CTC CCC AGC GTG ACC CTG GTC CAC AAA GGC AAC ATC ATG AAG TTC ACC    720
Leu Pro Ser Val Thr Leu Val His Lys Gly Asn Ile Met Lys Phe Thr
225                 230                 235                 240

GAA GGG GCC TTC CGG GAG TGG GGC TAC GCC CTG GCC CGG GAA AAG TAC    768
Glu Gly Ala Phe Arg Glu Trp Gly Tyr Ala Leu Ala Arg Glu Lys Tyr
                245                 250                 255

GGG GCC ACG CCC CTG GAC GGC GGG CCC TGG CAC GTC CTC AAA AAC CCC    816
Gly Ala Thr Pro Leu Asp Gly Gly Pro Trp His Val Leu Lys Asn Pro
        260                 265                 270

CGC ACC GGC AGG GAG ATC GTT ATC AAG GAC ATG ATG GCC GAC AAC TTC    864
Arg Thr Gly Arg Glu Ile Val Ile Lys Asp Met Met Ala Asp Asn Phe
        275                 280                 285

CTG CAG CAG ATC CTC CTC CGC CCC GAC GAA TAC TCG GTG ATC GCC ACC    912
Leu Gln Gln Ile Leu Leu Arg Pro Asp Glu Tyr Ser Val Ile Ala Thr
        290                 295                 300
```

TABLE 13

```
ATG AAC CTG AAC GGG GAC TAC ATC TCC GAT GCC CTG GCC GCC CAG GTG    960
Met Asn Leu Asn Gly Asp Tyr Ile Ser Asp Ala Leu Ala Ala Gln Val
305                 310                 315                 320

GGG GGC ATC GGC ATG GCC CCC GGG GCC AAC ATC AAC TAC AAG ACG GGC
1008
Gly Gly Ile Gly Met Ala Pro Gly Ala Asn Ile Asn Tyr Lys Thr Gly
                325                 330                 335

CAC GCC GTC TTT GAG GCC ACC CAC GGC ACC GCC CCC AAQ TAC GCT GGC
1056
His Ala Val Phe Glu Ala Thr His Gly Thr Ala Pro Lys Tyr Ala Gly
                340                 345                 350

CAG GAC AAG GTG AAC CCC AGC AGC GTC ATC CTC TCC GGG GAG ATG ATG
1104
Gln Asp Lys Val Asn Pro Ser Ser Val Ile Leu Ser Gly Glu Met Met
                355                 360                 365

CTT CGC TAC CTG GGC TGG AAC GAG GCG GCG GAC CTC ATC ATC AGG GCC   1152
Leu Arg Tyr Leu Gly Trp Asn Glu Ala Ala Asp Leu Ile Ile Arg Ala
        370                 375                 380

ATG GAG AGG ACC ATC AGC AAG GGC CTG GTC ACC TAC GAC TTC CAC CGC   1200
Met Glu Arg Thr Ile Ser Lys Gly Leu Val Thr Tyr Asp Phe His Arg
385                 390                 395                 400

CTC CTG GTG GCC GAG GGC AAG CCC GCC ACG CTT CTT AAG ACC AGC GAG   1248
Leu Leu Val Ala Glu Gly Lys Pro Ala Thr Leu Leu Lys Thr Ser Glu
                405                 410                 415

TTC GGC CAG GCC CTG ATC CAG CAC ATG GAC TGA                       1281
Phe Gly Gln Ala Leu Ile Gln His Met Asp ***
                420                 425
```

TABLE 14

Sequence ID No. 4
Sequence length: 1284
Sequence type: nucleic acid
Molecular type: double-strandedness
Topology: linear
Sequence species: another nucleic acid, synthetic DNA
Origin:
Name of organism: *Thermus aquaticus*
Name of strain: YTI (ATCC 25104)
Sequence characteristics
Symbol expressing the characteristics: structural gene
Method for identifying the characteristics: S
Sequence

| | | | | | | | | | | | | | | | | |
|---|---|---|---|---|---|---|---|---|---|---|---|---|---|---|---|---|
| ATG | GCT | TAC | CAG | CGC | ATC | CAG | ATT | CCG | CAG | GAG | GGC | GAA | AAG | ATC | ACC | 48 |
| Met | Ala | Tyr | Gln | Arg | Ile | Gln | Ile | Pro | Gln | Glu | Gly | Glu | Lys | Ile | Thr | |
| 1 | | | | 5 | | | | | 10 | | | | | 15 | | |
| ATC | CAA | GAG | GGC | GTC | CTG | AAG | GTG | CCG | GAC | CAG | CCC | ATC | ATC | GGC | TTC | 96 |
| Ile | Gln | Glu | Gly | Val | Leu | Lys | VaJ | Pro | Asp | Gln | Pro | Ile | Ile | Gly | Phe | |
| | | | 20 | | | | | 25 | | | | | 30 | | | |
| ATT | GAG | GGG | GAT | GGG | ACC | GGC | CCT | GAC | ATC | TGG | AGA | GCG | GCC | CAA | CCC | 144 |
| Ile | Glu | Gly | Asp | Gly | Thr | Gly | Pro | Asp | Ile | Trp | Arg | Ala | Ala | Gln | Pro | |
| | | 35 | | | | | 40 | | | | | 45 | | | | |

TABLE 15

| | | | | | | | | | | | | | | | | |
|---|---|---|---|---|---|---|---|---|---|---|---|---|---|---|---|---|
| GTC | CTA | GAC | GCC | GCC | GTG | GCC | AAA | GCC | TAC | GGC | GGG | CAA | CGG | CGC | ATC | 192 |
| Val | Leu | Asp | Ala | Ala | Val | Ala | Lys | Ala | Tyr | Gly | Gly | Gln | Arg | Arg | Ile | |
| | 50 | | | | | 55 | | | | | 60 | | | | | |
| GTC | TGG | GTG | GAG | CTT | TAC | GCC | GGG | GAA | AAG | GCC | AAC | CAG | GTC | TAC | GGG | 240 |
| Val | Trp | Val | Glu | Leu | Tyr | Ala | Gly | Glu | Lys | Ala | Asn | Gln | Val | Tyr | Gly | |
| 65 | | | | | 70 | | | | | 75 | | | | | 80 | |
| GAG | CCC | ATC | TGG | CTC | CCC | GAG | GAG | ACC | CTG | GAG | TTC | ATC | CGG | GAG | TAC | 288 |
| Glu | Pro | Ile | Trp | Leu | Pro | Glu | Glu | Thr | Leu | Glu | Phe | Jle | Arg | Glu | Tyr | |
| | | | 85 | | | | | 90 | | | | | 95 | | | |
| CTG | GTG | GCC | ATC | AAG | GGC | CCC | CTG | ACC | ACG | CCG | GTG | GGC | GGC | GGC | ATC | 336 |
| Leu | Val | Ala | Ile | Lys | Gly | Pro | Leu | Thr | Thr | Pro | Val | Gly | Gly | Gly | Ile | |
| | | | 100 | | | | | 105 | | | | | 110 | | | |
| CGG | AGC | ATC | AAC | GTG | GCC | CTC | AGG | CAG | GAG | CTG | GAC | CTC | TAC | GCC | TGC | 384 |
| Arg | Ser | Ile | Asn | Val | Ala | Leu | Arg | Gln | Glu | Leu | Asp | Leu | Tyr | Ala | Cys | |
| | | 115 | | | | | 120 | | | | | 125 | | | | |
| GTG | CGC | CCC | GTG | CGC | TGG | TTC | CAG | GGG | GTG | CCC | AGT | CCG | GTG | AAG | CAC | 432 |
| Val | Arg | Pro | Val | Arg | Trp | Phe | Gln | Gly | Val | Pro | Ser | Pro | Val | Lys | His | |
| | | 130 | | | | | 135 | | | | | 140 | | | | |
| CCG | GAG | CTG | GTC | AAC | ATG | GTC | ATC | TTC | CGG | GAG | AAC | ACC | GAG | GAC | ATC | 480 |
| Pro | Glu | Leu | Val | Asn | Met | Val | Jle | Phe | Arg | Glu | Asn | Thr | Glu | Asp | Ile | |
| 145 | | | | | 150 | | | | | 155 | | | | | 160 | |
| TAC | GCC | GGG | ATT | GAG | IGG | CCG | GCG | GGG | AGC | GAG | GAG | GTA | AAG | AAG | GTC | 528 |
| Tyr | Ala | Gly | Ile | Glu | Trp | Pro | Ala | Gly | Ser | Glu | Glu | Val | Lys | Lys | Val | |
| | | | 165 | | | | | 170 | | | | | 175 | | | |

TABLE 16

| | | | | | | | | | | | | | | | | |
|---|---|---|---|---|---|---|---|---|---|---|---|---|---|---|---|---|
| CTA | GAC | TTC | TTG | AAG | CGG | GAG | TTC | CCC | AAG | GCC | TAC | GCC | AAG | ATC | CGC | 576 |
| Leu | Asp | Phe | Leu | Lys | Arg | Glu | Phe | Pro | Lys | Ala | Tyr | Ala | Lys | Ile | Arg | |
| | | | 180 | | | | | 185 | | | | | 190 | | | |
| TTC | CCC | GAG | ACC | TCG | GGC | CTG | GGC | CTG | AAG | CCC | ATC | TCC | AAG | GAG | GGC | 624 |
| Phe | Pro | Glu | Thr | Ser | Gly | Leu | Gly | Leu | Lys | Pro | Ile | Ser | Lys | Glu | Gly | |
| | | 195 | | | | | 200 | | | | | 205 | | | | |
| ACG | GAG | CGC | CTG | GTG | GAG | GCG | GCC | ATT | GAG | TAC | GCC | ATC | AAG | GAG | GAC | 672 |
| Thr | Glu | Arg | Leu | Val | Glu | Ala | Ala | Ile | Glu | Tyr | Ala | Ile | Lys | Glu | Asp | |
| | | 210 | | | | | 215 | | | | | 220 | | | | |

TABLE 16-continued

| | | | | | | | | | | | | | | | |
|---|---|---|---|---|---|---|---|---|---|---|---|---|---|---|---|
| CTC | CCC | AGC | GTG | ACC | CTG | GTC | CAC | AAA | GGC | AAC | ATC | ATG | AAG | TTC | ACC | 720 |
| Leu | Pro | Ser | Val | Thr | Leu | Val | His | Lys | Gly | Asn | Ile | Met | Lys | Phe | Thr | |
| 225 | | | | | 230 | | | | | 235 | | | | | 240 | |

| | | | | | | | | | | | | | | | |
|---|---|---|---|---|---|---|---|---|---|---|---|---|---|---|---|
| GAA | GGG | GCC | TTC | CGG | GAG | TGG | GGC | TAC | GCC | CTG | GCC | CGG | GAA | AAG | TAC | 768 |
| Glu | Gly | Ala | Phe | Arg | Glu | Trp | Gly | Tyr | Ala | Leu | Ala | Arg | Glu | Lys | Tyr | |
| | | | | 245 | | | | | 250 | | | | | 255 | | |

| | | | | | | | | | | | | | | | |
|---|---|---|---|---|---|---|---|---|---|---|---|---|---|---|---|
| GGG | GCC | ACG | CCC | CTG | GAC | GGC | GGG | CCC | TGG | CAC | GTC | CTC | AAA | AAC | CCC | 816 |
| Gly | Ala | Thr | Pro | Leu | Asp | Gly | Gly | Pro | Trp | His | Val | Leu | Lys | Asn | Pro | |
| | | | 260 | | | | | 265 | | | | | 270 | | | |

| | | | | | | | | | | | | | | | |
|---|---|---|---|---|---|---|---|---|---|---|---|---|---|---|---|
| CGC | ACC | GGC | AGG | GAG | ATC | GTT | ATC | AAG | GAC | ATG | ATC | GCC | GAC | AAC | TTC | 864 |
| Arg | Thr | Gly | Arg | Glu | Ile | Val | Ile | Lys | Asp | Met | Jle | Ala | Asp | Asn | Phe | |
| | | 275 | | | | | 280 | | | | | 285 | | | | |

| | | | | | | | | | | | | | | | |
|---|---|---|---|---|---|---|---|---|---|---|---|---|---|---|---|
| CTG | CAG | CAG | ATC | CTC | CTC | CGC | CCC | GAC | GAA | TAC | TCG | GTG | ATC | GCC | ACC | 912 |
| Leu | Gln | Gln | Ile | Leu | Leu | Arg | Pro | Asp | Glu | Tyr | Ser | Val | Ile | Ala | Thr | |
| | 290 | | | | | 295 | | | | | 300 | | | | | |

TABLE 17

| | | | | | | | | | | | | | | | |
|---|---|---|---|---|---|---|---|---|---|---|---|---|---|---|---|
| ATG | AAC | CTG | AAC | GGG | GAC | TAC | ATC | TCC | GAT | GCC | CTG | GCC | GCC | CAG | GTG | 960 |
| Met | Asn | Leu | Asn | Gly | Asp | Tyr | Ile | Ser | Asp | Ala | Leu | Ala | Ala | Gln | Val | |
| 305 | | | | | 310 | | | | | 315 | | | | | 320 | |

| | | | | | | | | | | | | | | | |
|---|---|---|---|---|---|---|---|---|---|---|---|---|---|---|---|
| GGG | GGC | ATC | GGC | ATC | GCC | CCC | GGG | GCC | AAC | ATC | AAC | TAC | AAG | ACG | GGC | 1008 |
| Gly | Gly | Ile | Gly | Ile | Ala | Pro | Gly | Ala | Asn | Ile | Asn | Tyr | Lys | Thr | Gly | |
| | | | | 325 | | | | | 330 | | | | | 335 | | |

| | | | | | | | | | | | | | | | |
|---|---|---|---|---|---|---|---|---|---|---|---|---|---|---|---|
| CAC | GCC | GTC | TTT | GAG | GCC | ACC | CAC | GGC | ACC | GCC | CCC | AAG | TAC | GCT | GGC | 1056 |
| His | Ala | Val | Phe | Glu | Ala | Thr | His | Gly | Thr | Ala | Pro | Lys | Tyr | Ala | Gly | |
| | | | 340 | | | | | 345 | | | | | 350 | | | |

| | | | | | | | | | | | | | | | |
|---|---|---|---|---|---|---|---|---|---|---|---|---|---|---|---|
| CAG | GAC | AAG | GTG | AAC | CCC | AGC | AGC | GTC | ATC | CTC | TCC | GGG | GAG | ATG | ATG | 1104 |
| Gln | Asp | Lys | Val | Asn | Pro | Ser | Ser | Val | Ile | Leu | Ser | Gly | Glu | Met | Met | |
| | | 355 | | | | | 360 | | | | | 365 | | | | |

| | | | | | | | | | | | | | | | |
|---|---|---|---|---|---|---|---|---|---|---|---|---|---|---|---|
| CTT | CGC | TAC | CTG | GGC | TGG | AAC | GAG | GCG | GCG | GAC | CTC | ATC | ATC | AGG | GCC | 1152 |
| Leu | Arg | Tyr | Leu | Gly | Trp | Asn | Glu | Ala | Ala | Asp | Leu | Ile | Jle | Arg | Ala | |
| | 370 | | | | | 375 | | | | | 380 | | | | | |

| | | | | | | | | | | | | | | | |
|---|---|---|---|---|---|---|---|---|---|---|---|---|---|---|---|
| ATG | GAG | AGG | ACC | ATC | AGC | AAG | GGC | CTG | GTC | ACC | TAC | GAC | TTC | CAC | CGC | 1200 |
| Met | Glu | Arg | Thr | Ile | Ser | Lys | Gly | Leu | Val | Thr | Tyr | Asp | Phe | His | Arg | |
| 385 | | | | | 390 | | | | | 395 | | | | | 400 | |

| | | | | | | | | | | | | | | | |
|---|---|---|---|---|---|---|---|---|---|---|---|---|---|---|---|
| CTC | CTG | GTG | GCC | GAG | GGC | AAG | CCC | GCC | ACG | CTT | CTT | AAG | ACC | AGC | GAG | 1248 |
| Leu | Leu | Val | Ala | Glu | Gly | Lys | Pro | Ala | Thr | Leu | Leu | Lys | Thr | Ser | Glu | |
| | | | | 405 | | | | | 410 | | | | | 415 | | |
| TTC | GGC | CAG | GCC | CTG | ATC | CAG | CAC | ATG | GAC | TAA | TGA | | | | | 1284 |
| Phe | Gty | Gln | Ala | Leu | Ile | Gln | His | Met | Asp | *** | *** | | | | | |
| | | 420 | | | | | 425 | | | | | | | | | |

---

What is claimed is:

1. An ammonia elimination reagent in a buffer solution, which comprises isocitrate dehydrogenase, 2-oxoglutaric acid, reduced nicotinamide adenine dinucleotide (NADH), isocitric acid, glutamate dehydrogenase, and magnesium or manganese ions, wherein the isocitrate dehydrogenase is an isocitrate dehydrogenase prepared by a method comprising:

(1) preparing an expression vector comprising a modified nucleotide sequence of codon Nos. 1 to 427 in SEQ ID NO:2, wherein the modification is at least one replacement selected from the group consisting of (a) replacement of codon No. 2 (GCC) by a codon selected from the codon group consisting of GCT, GCA, and GCG, and (b) replacement of codon No. 9 (CCC) by a codon selected from the codon group consisting of CCT, CCA, and CCG;

(2) transforming a microorganism by using the prepared expression vector;

(3) culturing the obtained transformant in a medium; and (4) recovering isocitrate dehydrogenase from the resulting medium.

2. The ammonia elimination reagent in a buffer solution according to claim 1, wherein the modified nucleotide sequence in step (1) has been further modified by replacement of codon No. 427 (TGA) by a codon selected from the codon group consisting of TAA, and TAATAG.

3. The ammonia elimination reagent in a buffer solution according to claim 1, wherein the modified nucleotide sequence is the nucleotide sequence of SEQ ID NO:3.

4. The ammonia elimination reagent in a buffer solution according to claim 2, wherein the modified nucleotide sequence is the nucleotide sequence of SEQ ID NO:4.

5. The ammonia elimination reagent in a buffer solution according to claim 1, wherein the microorganism in step (2) is *Escherichia coli*.

6. The ammonia elimination reagent in a buffer solution according to claim 4, wherein the obtained transformant in step (3) is *Echerichia coli* JM109/pTRP-Taq ICD, FERM BP-6365.

* * * * *